US012559926B2

(12) United States Patent
Tabei et al.

(10) Patent No.: US 12,559,926 B2
(45) Date of Patent: Feb. 24, 2026

(54) SANITARY WASHING DEVICE AND TOILET DEVICE

(71) Applicant: TOTO LTD., Kitakyushu (JP)

(72) Inventors: Hitomi Tabei, Kitakyushu (JP);
Toshinari Yaoka, Kitakyushu (JP)

(73) Assignee: TOTO LTD., Kitakyushu (JP)

( * ) Notice: Subject to any disclaimer, the term of this patent is extended or adjusted under 35 U.S.C. 154(b) by 75 days.

(21) Appl. No.: 18/602,341

(22) Filed: Mar. 12, 2024

(65) Prior Publication Data

US 2024/0401320 A1     Dec. 5, 2024

(30) Foreign Application Priority Data

May 31, 2023     (JP) ................................. 2023-089923

(51) Int. Cl.
E03D 9/08        (2006.01)
A61L 2/10        (2006.01)

(52) U.S. Cl.
CPC .................. E03D 9/08 (2013.01); A61L 2/10 (2013.01); *A61L 2202/11* (2013.01)

(58) Field of Classification Search
CPC .. E03D 9/08; E03D 9/00; E03D 9/005; E03D 11/02; A61L 2/10; A61L 2202/11
USPC .................................. 4/420, 420.4, 447–448
See application file for complete search history.

(56) References Cited

U.S. PATENT DOCUMENTS

| | | | | |
|---|---|---|---|---|
| 8,365,317 B1 * | 2/2013 | Dorra | ................... | A47K 13/302 4/444 |
| 8,701,222 B2 * | 4/2014 | Shin | .......................... | E03D 9/08 4/443 |
| 11,668,084 B2 * | 6/2023 | Yamamura | ................ | E03D 9/08 4/447 |
| 11,692,337 B2 * | 7/2023 | Gupta | ....................... | B05B 9/03 4/448 |

(Continued)

FOREIGN PATENT DOCUMENTS

| | | | | | |
|---|---|---|---|---|---|
| EP | | 3168378 A2 * | 5/2017 | ............. | E03D 11/02 |
| JP | | 2008038475 A * | 2/2008 | ............. | E03D 11/02 |

(Continued)

OTHER PUBLICATIONS

Notice of Reasons for Refusal for Japanese Patent Application No. 2023-089923 dated Mar. 5, 2025.

*Primary Examiner* — Lori L Baker
(74) *Attorney, Agent, or Firm* — McDonald Hopkins LLC

(57)        ABSTRACT

A sanitary washing device is mounted on a flush toilet. The flush toilet includes a bowl. The bowl receives human waste. The sanitary washing device includes a private part washing nozzle, a casing, and a light-irradiating part. The private part washing nozzle is configured to advance and retreat. The private part washing nozzle includes a water discharge port. The water discharge port discharges wash water toward a private part of a user. The casing includes a nozzle storage part. The nozzle storage part is configured to store the private part washing nozzle when the private part washing nozzle is retracted. The light-irradiating part irradiates a (Continued)

bacteria-removing light. The bacteria-removing light is light having a bacteria-removing action. The bacteria-removing light is irradiated from the light-irradiating part simultaneously on the nozzle storage part and the bowl.

6 Claims, 11 Drawing Sheets

(56) References Cited

U.S. PATENT DOCUMENTS

| | | | | |
|---|---|---|---|---|
| 11,713,566 B2 * | 8/2023 | Gupta | ..................... | E03D 9/005 |
| | | | | 4/448 |
| 11,739,518 B2 * | 8/2023 | Shiohara | ................. | E03D 11/13 |
| | | | | 4/420 |
| 2007/0256226 A1 | 11/2007 | Pinizzotto | | |
| 2014/0101838 A1 * | 4/2014 | Gupta | ..................... | B05B 15/16 |
| | | | | 4/448 |
| 2014/0352049 A1 * | 12/2014 | Nakamura | ................ | E03D 9/08 |
| | | | | 4/448 |
| 2018/0347169 A1 * | 12/2018 | Tsujita | .................... | G01S 13/56 |
| 2019/0368180 A1 | 12/2019 | Yaoka et al. | | |
| 2021/0164212 A1 | 6/2021 | Baba et al. | | |
| 2023/0100608 A1 * | 3/2023 | Smith | ....................... | E03D 9/08 |
| | | | | 4/448 |

FOREIGN PATENT DOCUMENTS

| | | | | | | |
|---|---|---|---|---|---|---|
| JP | 2011127320 A | * | 6/2011 | ............. | E03D 11/02 |
| JP | 2013-209861 A | | 10/2013 | | |
| JP | 2017-008605 A | | 1/2017 | | |
| JP | 2017-008607 A | | 1/2017 | | |
| JP | 2019-210801 A | | 12/2019 | | |
| JP | 2020-186531 A | | 11/2020 | | |
| JP | 2021085314 A | * | 6/2021 | .............. | A61L 2/10 |
| JP | 2022-180742 A | | 12/2022 | | |
| KR | 10-2011-0131898 A | | 12/2011 | | |

* cited by examiner

UP

BACK ← → FRONT

DOWN

BACK

RIGHT ← → LEFT

FRONT

SANITARY WASHING DEVICE AND TOILET DEVICE

CROSS-REFERENCE TO RELATED APPLICATIONS

This application is based upon and claims the benefit of priority from Japanese Patent Application No. 2023-089923, filed on May 31, 2023; the entire contents of which are incorporated herein by reference.

FIELD

Embodiments described herein relate generally to a sanitary washing device and a toilet device.

BACKGROUND

In a toilet device known in the art, the nozzle storage part inside the casing and the bowl outside the casing are prone to visible stains caused by bacterial growth. In such a toilet device, for example, technology is known to suppress bacterial growth and visible stains by irradiating bacteria-removing light such as ultraviolet or the like on parts prone to bacterial growth (e.g., 2020-186531 JP A). Bacteria become visible stains when the bacteria count per unit area exceeds a certain value. Generally, the intensity of bacterial growth suppression by ultraviolet irradiation is represented by the integrated irradiance, which is the product of the irradiance and the irradiation time. For an initial bacteria count taken to be the bacteria count per unit area when starting the ultraviolet irradiation, the occurrence of visible stains can be suppressed by suppressing bacterial growth with ultraviolet irradiation so that the initial bacteria count does not increase to a bacteria count resulting in visible stains.

In conventional art, 2020-186531 JP A addresses the problem of sterilizing inside the nozzle storage part with ultraviolet but not being able to sterilize the surface of the bowl by making it possible to irradiate ultraviolet on both the nozzle storage part and the bowl with a common light-irradiating part by moving the light-irradiating part irradiating ultraviolet in the casing interior and the bowl. Thus, according to 2020-186531 JP A, compared to when light-irradiating parts are provided respectively for the nozzle storage part and the bowl to be irradiated, the cost is reduced by sharing the light-irradiating part.

However, the toilet device according to 2020-186531 JP A is problematic in that it takes time to complete the irradiation sequence because the use of a common light-irradiating part makes it necessary to irradiate ultraviolet sequentially on the nozzle storage part and bowl. Bacteria proliferate by division by a power of two over time. That is, if the irradiation is slow, the bacteria count that must be killed (the initial bacteria count) proliferates by a power of two with respect to the elapsed time. Generally, the effectiveness of bacterial growth suppression by light irradiation is represented by the orders of magnitude that the bacteria count is reduced per integrated irradiance. For example, bacterial growth suppression by irradiating sterilizing rays of 5 mJ/cm² provides a reduction of three orders of magnitude. Because the bacteria count must be maintained at or below a prescribed value to suppress visible stains, the integrated irradiance necessary to keep the bacteria count at or below the prescribed value increases as the initial bacteria count increases. By starting the irradiation of light as soon as possible after the bacteria adheres, a lower integrated irradiance can be used to reduce the bacteria count to the prescribed value or less (or maintain the bacteria count at or below the prescribed value) to suppress the visible stains.

SUMMARY

According to the embodiment, a sanitary washing device is mounted on a flush toilet. The flush toilet includes a bowl. The bowl receives human waste. The sanitary washing device includes a private part washing nozzle, a casing, and a light-irradiating part. The private part washing nozzle is configured to advance and retreat. The private part washing nozzle includes a water discharge port. The water discharge port discharges wash water toward a private part of a user. The casing includes a nozzle storage part. The nozzle storage part is configured to store the private part washing nozzle when the private part washing nozzle is retracted. The light-irradiating part irradiates a bacteria-removing light. The bacteria-removing light is light having a bacteria-removing action. The bacteria-removing light is irradiated from the light-irradiating part simultaneously on the nozzle storage part and the bowl.

DETAILED DESCRIPTION

Figure 1:
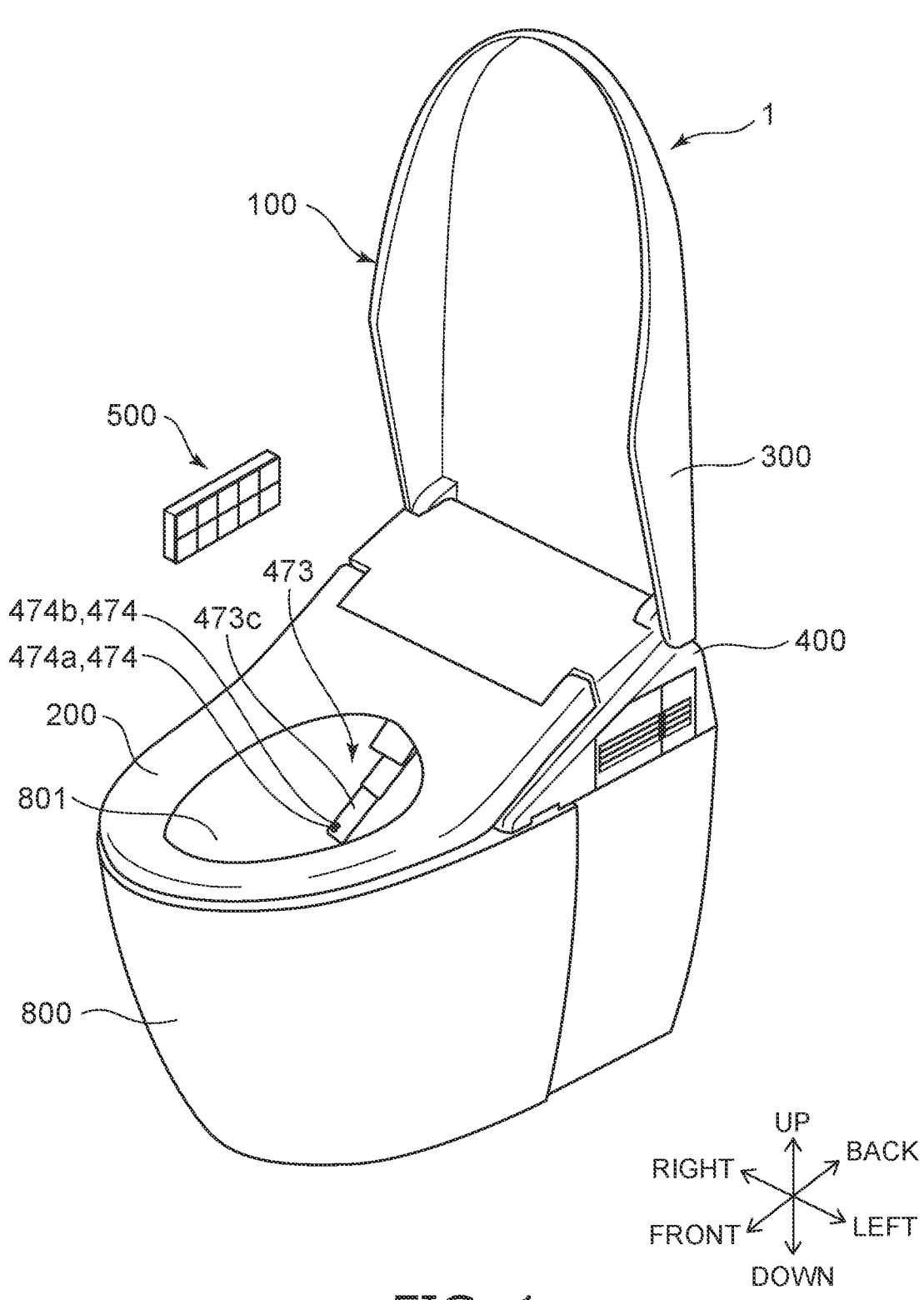
FIG. 1 is a perspective view showing a toilet device according to an embodiment.

A first aspect is a sanitary washing device including a private part washing nozzle, a casing, and a light-irradiating part; the sanitary washing device is mounted on a flush toilet including a bowl receiving human waste; the private part washing nozzle advances and retreats, and includes a water discharge port discharging wash water toward a private part of a user; the casing includes a nozzle storage part configured to store the private part washing nozzle when the private part washing nozzle is retracted; the light-irradiating part irradiates a bacteria-removing light; the bacteria-removing light has a bacteria-removing action; and the bacteria-removing light is irradiated from the light-irradiating part simultaneously on the nozzle storage part and the bowl.

According to the sanitary washing device, a cost increase can be prevented by irradiating the bacteria-removing light on the nozzle storage part and the bowl from a common light-irradiating part. By irradiating the bacteria-removing light simultaneously on the nozzle storage part and the bowl, the irradiation of the bacteria-removing light can be started while the initial bacteria count adhered to the nozzle storage part and the bowl is as low as possible. Therefore, the integrated irradiance necessary to suppress bacterial growth can be reduced. For the same irradiance, the prescribed integrated irradiance can be reached and bacterial growth can be suppressed in a shorter period of time by starting the irradiation simultaneously instead of sequentially. Accordingly, bacterial growth in the nozzle storage part and the bowl can be suppressed by irradiating the bacteria-removing light in a short period of time while preventing a cost increase due to an increase of light-irradiating parts. As a result, stains are suppressed, and a hygienic sanitary washing device can be provided.

A second aspect is the sanitary washing device of the first aspect, wherein an average value of an irradiance of an inner surface of the nozzle storage part irradiated with the bacteria-removing light is greater than an average value of an irradiance of a surface of the bowl irradiated with the bacteria-removing light.

Among the irradiation objects of the bacteria-removing light, the nozzle storage part is inside the casing; and the bowl is outside the casing. The bowl is washed each time the toilet device (the flush toilet) is used by the user. On the other hand, for example, when a male urinates standing up, the private part washing nozzle and the nozzle storage part are not washed because the private part washing nozzle is not used. That is, the bacteria count is easily reduced in the bowl because the bacteria are rinsed away by washing each time the toilet device is used. In contrast, it is difficult to reduce the bacteria count in the nozzle storage part because there are cases where the toilet device is used but the nozzle storage part is not washed. Therefore, there are cases where the nozzle storage part has a greater bacteria count than the bowl. The integrated irradiance necessary to suppress bacterial growth increases as the bacteria count increases. Therefore, by setting the average value of the irradiance of the inner surface of the nozzle storage part irradiated with the bacteria-removing light to be greater than the average value of the irradiance of the surface of the bowl irradiated with the bacteria-removing light, the intensity of the bacteria removal at the nozzle storage part, which tends to have a greater bacteria count than the bowl, can be set to be greater than the intensity of the bacteria removal at the bowl. Accordingly, bacterial growth at the nozzle storage part and bowl can be efficiently suppressed. The occurrence of stains on the nozzle storage part and the bowl can be efficiently suppressed thereby.

A third aspect is the sanitary washing device of the first aspect, wherein the light-irradiating part is disposed inside the casing.

4

Compared with the bowl, the nozzle storage part is washed less frequently and may have a greater bacteria count. The integrated irradiance necessary to suppress bacterial growth increases as the bacteria count increases. Generally, for light sources other than lasers, the irradiance radiated from the light source increases as the distance decreases. By disposing the light-irradiating part inside the casing, the bacteria-removing light can be irradiated on the nozzle storage part with a larger irradiance than the bowl. Therefore, by disposing the light-irradiating part inside the casing, even when the bacteria-removing light is irradiated from a common light-irradiating part simultaneously on the bowl and the nozzle storage part, which tends to have a greater bacteria count than the bowl, the irradiation time of the bacteria-removing light can be reduced because the difference between the time to reduce the bacteria count of the nozzle storage part to or below a prescribed value and the time to reduce the bacteria count of the bowl to or below the prescribed value can be reduced.

A fourth aspect is the sanitary washing device of the first aspect, wherein the bowl includes a bowl back part and a bowl front part; when referenced to an anus washing position, the bowl back part is positioned behind the anus washing position, and the bowl front part is positioned frontward of the anus washing position; and an average value of an irradiance of a surface of the bowl back part irradiated with the bacteria-removing light is greater than an average value of an irradiance of a surface of the bowl front part irradiated with the bacteria-removing light.

As described above, the integrated irradiance necessary to cause the bacteria count to be not more than a prescribed value also increases as the bacteria count increases. The anus washing position is the general anus position when the user is seated on the toilet seat. The user that is seated on the toilet seat defecates in a forward-tilted posture. Therefore, organic substances included in the feces are likely to adhere to the bowl back part positioned behind the anus washing position. In other words, the bowl back part has a greater initial bacteria count than the bowl front part because organic substances, which nourish bacteria and create an environment favorable for bacterial growth, tend to adhere to the bowl back part. As a result, by setting the average value of the irradiance of the surface of the bowl back part irradiated with the bacteria-removing light to be greater than the average value of the irradiance of the surface of the bowl front part irradiated with the bacteria-removing light, the bacteria removal intensity at the bowl back part, which tends to have a greater initial bacteria count than the bowl front part, can be set to be greater than the bacteria removal intensity at the bowl front part. Accordingly, the bacterial growth at the bowl back part and the bowl front part can be efficiently suppressed. As a result, the difference can be reduced between the time to set the bacteria count to be not more than the prescribed value at the bowl back part and the time to set the bacteria count to be not more than the prescribed value at the bowl front part even when a common light-irradiating part irradiates the bacteria-removing light simultaneously on the bowl front part and the bowl back part, which tends to have a greater initial bacteria count than the bowl front part; therefore, the irradiation time of the bacteria-removing light can be reduced, and the occurrence of stains at the bowl can be efficiently suppressed.

A fifth aspect is a toilet device including the sanitary washing device according to any one of the first to fourth aspects, and including the flush toilet.

According to the toilet device, a cost increase can be prevented by irradiating the bacteria-removing light on the nozzle storage part and the bowl from the common light-irradiating part. By irradiating the bacteria-removing light simultaneously on the nozzle storage part and the bowl, bacterial growth can be suppressed by a shorter irradiation than when irradiating the bacteria-removing light sequentially. Accordingly, bacterial growth at the nozzle storage part and bowl can be suppressed by irradiating the bacteria-removing light in a short period of time while preventing a cost increase due to an increase of light-irradiating parts. As a result, the occurrence of stains can be suppressed, and a hygienic toilet device can be provided.

Embodiments of the invention will now be described with reference to the drawings.

FIG. 1 is a perspective view showing a toilet device according to an embodiment.

As illustrated in FIG. 1, the toilet device 1 includes a flush toilet 800, and a sanitary washing device 100 mounted on the flush toilet 800. The flush toilet 800 is a so-called sit-down flush toilet. The flush toilet 800 includes a bowl 801 that receives human waste. The flush toilet 800 is described below.

The sanitary washing device 100 includes a casing 400, a toilet seat 200, and a toilet lid 300. The toilet seat 200 and the toilet lid 300 each are pivotally supported to be openable and closable with respect to the casing 400.

In this specification, up/upward/above/higher than, down/downward/below/lower than, front/frontward/forward, back/backward/behind, right, and left when viewed by a user seated on the toilet seat 200 with the back of the user facing the toilet lid are referred 300 respectively to as "up/upward/above/higher than", "down/downward/below/lower than", "front/frontward/forward", "back/backward/behind", "right", and "left".

A body wash function part that washes a "bottom" or the like of the user sitting on the toilet seat 200, etc., are embedded inside the casing 400. For example, a seating detection sensor 404 (see FIG. 2) that detects the user being seated on the toilet seat 200 is disposed inside the casing 400. When the seating detection sensor 404 detects the user sitting on the toilet seat 200, the user can operate an operation unit 500 such as, for example, a remote control or the like to advance a private part washing nozzle (hereinbelow, called simply the "nozzle" for convenience of description) 473 into the bowl 801 of the flush toilet 800 and retract the nozzle 473 from the interior of the bowl 801. The state in which the nozzle 473 is advanced into the bowl 801 is illustrated in the sanitary washing device 100 illustrated in FIG. 1.

One or multiple water discharge ports 474 are provided in the tip portion of the nozzle 473. The water discharge port 474 discharges wash water toward a private part of the user. The nozzle 473 can wash the private part such as the "bottom" or the like of the user sitting on the toilet seat 200 by spraying water from the water discharge port 474 provided in the tip portion.

Figure 2:
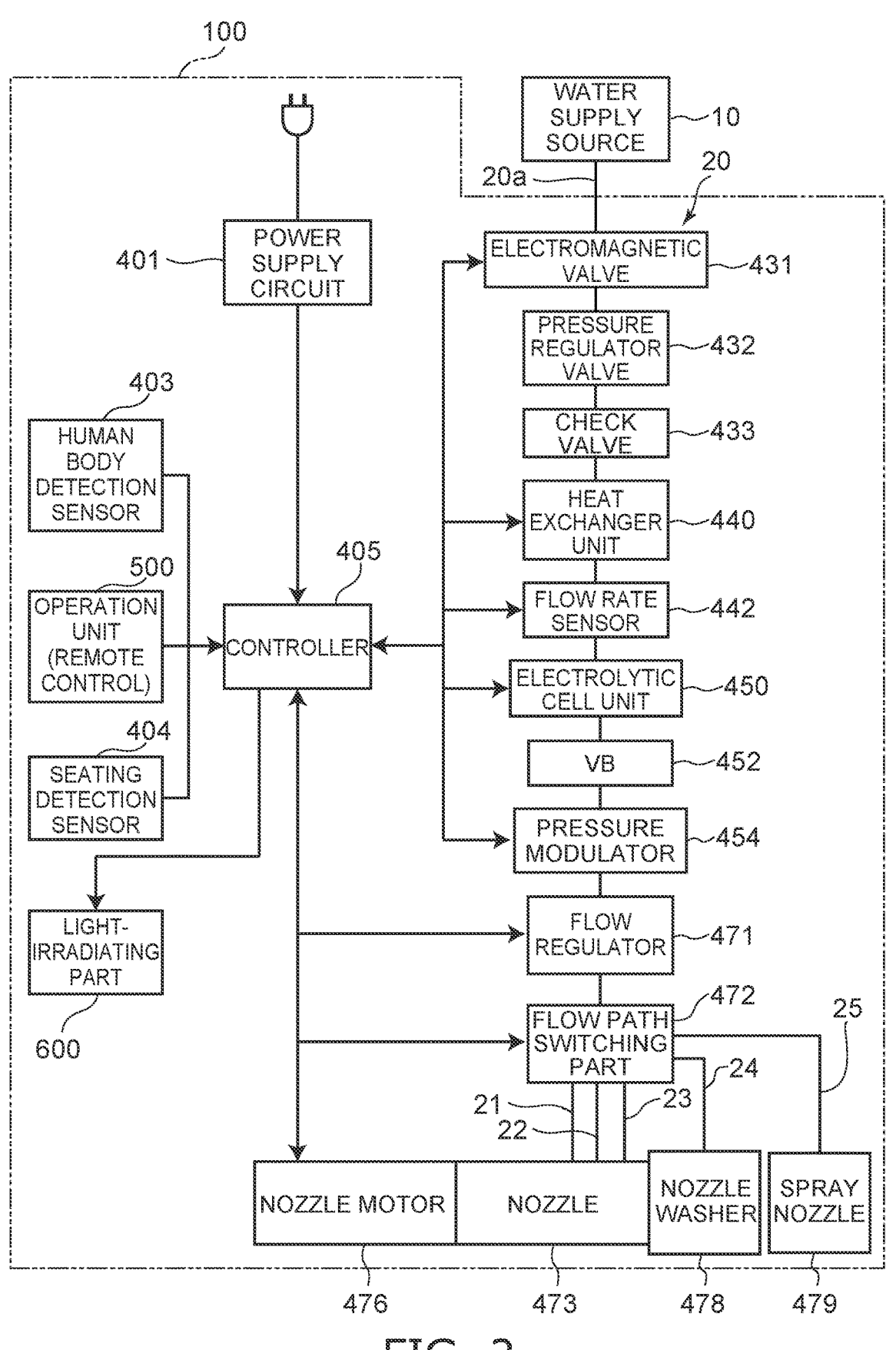
FIG. 2 is a block diagram showing the relevant components of the sanitary washing device according to the embodiment.

FIG. 2 is a block diagram showing the relevant components of the sanitary washing device according to the embodiment.

FIG. 2 illustrates relevant components of both a water channel system and an electrical system.

As illustrated in FIG. 2, the sanitary washing device 100 includes a water transfer part 20. The water transfer part 20 includes a pipe line 20a that reaches the nozzle 473 from a water supply source 10 such as a service water line, a water storage tank, etc. The water transfer part 20 guides the water supplied from the water supply source 10 to the nozzle 473 via the pipe line 20a. For example, the pipe line 20a is formed of components such as an electromagnetic valve 431, a heat exchanger unit 440, a flow path switching part 472, etc., which are described below, and multiple piping that connects these components.

The electromagnetic valve 431 is disposed at the upstream side of the water transfer part 20. The electromagnetic valve 431 is an openable and closable electromagnetic valve and controls the supply of the water based on a command from a controller 405 disposed inside the casing 400. In other words, the electromagnetic valve 431 opens and closes the pipe line 20a. The water that is supplied from the water supply source 10 is caused to flow in the pipe line 20a by setting the electromagnetic valve 431 to the open state.

A pressure regulator valve 432 is disposed downstream of the electromagnetic valve 431. The pressure regulator valve 432 regulates the pressure inside the pipe line 20a to be in a prescribed pressure range when the water supply pressure is high. A check valve 433 is disposed downstream of the pressure regulator valve 432. The check valve 433 suppresses the backflow of water toward the upstream side of the check valve 433 when the pressure inside the pipe line 20a decreases, etc.

The heat exchanger unit 440 (the heater) is disposed downstream of the check valve 433. The heat exchanger unit 440 includes a heater and heats the water supplied from the water supply source 10 to, for example, a specified temperature. In other words, the heat exchanger unit 440 produces warm water.

The heat exchanger unit 440 is, for example, an instant heating-type (instantaneous-type) heat exchanger that uses a ceramic heater, etc. Compared to a warm water storage heating-type heat exchanger that uses a warm water storage tank, the instant heating-type heat exchanger can heat the water to the specified temperature in a short period of time. The heat exchanger unit 440 is not limited to an instant heating-type heat exchanger and may be a warm water storage heating-type heat exchanger. The heater is not limited to a heat exchanger; for example, another heating technique such as one that utilizes microwave heating, etc., may be used.

The heat exchanger unit 440 is connected with the controller 405. For example, the controller 405 heats the water to a temperature set by the operation unit 500 by controlling the heat exchanger unit 440 according to an operation of the operation unit 500 by the user.

A flow rate sensor 442 is disposed downstream of the heat exchanger unit 440. The flow rate sensor 442 detects the flow rate of the water discharged from the heat exchanger unit 440. In other words, the flow rate sensor 442 detects the flow rate of the water flowing through the pipe line 20a. The flow rate sensor 442 is connected to the controller 405. The flow rate sensor 442 inputs the detection result of the flow rate to the controller 405.

An electrolytic cell unit 450 is disposed downstream of the flow rate sensor 442. The electrolytic cell unit 450 generates a liquid (functional water) including hypochlorous acid from the tap water by electrolyzing the tap water flowing through the interior of the electrolytic cell unit 450. The electrolytic cell unit 450 is connected to the controller 405. The electrolytic cell unit 450 generates the bacteria-removing water (the functional water) based on a control by the controller 405.

The functional water that is generated by the electrolytic cell unit 450 may be, for example, a solution including metal ions such as silver ions, copper ions, etc. The functional water that is generated by the electrolytic cell unit 450 may be a solution including electrolytic chlorine, ozone, etc. Or, the functional water that is generated by the electrolytic cell unit 450 may be acidic water or alkaline water.

A vacuum breaker (VB) 452 is disposed downstream of the electrolytic cell unit 450. The vacuum breaker 452 includes, for example, a flow channel for allowing the water to flow, an intake for drawing air into the flow channel, and a valve mechanism that opens and closes the intake. For example, the valve mechanism blocks the intake when water is flowing in the flow channel and draws air into the flow channel by opening the intake when the flow of the water stops. In other words, the vacuum breaker 452 draws air into the pipe line 20*a* when the water does not flow in the water transfer part 20. The valve mechanism includes, for example, a float valve.

As described above, the vacuum breaker 452 draws air into the pipe line 20*a*, thereby promoting, for example, water drainage of the part of the pipe line 20*a* downstream of the vacuum breaker 452. For example, the vacuum breaker 452 promotes the water drainage of the nozzle 473. Thus, the vacuum breaker 452 drains the water inside the nozzle 473 and draws air into the nozzle 473, thereby suppressing, for example, the undesirable backflow of the water supply source 10 (the fresh water) side of the wash water inside the nozzle 473, the liquid waste collected inside the bowl 801, etc.

A pressure modulator 454 is disposed downstream of the vacuum breaker 452. The pressure modulator 454 applies a pulsatory motion to the water discharged from the nozzle 473 and/or a water discharger 478*a* of a nozzle washer 478 by applying a pulsatory motion or an acceleration to the flow of the water inside the pipe line 20*a* of the water transfer part 20. In other words, the pressure modulator 454 causes the fluidic state of the water flowing through the pipe line 20*a* to fluctuate. The pressure modulator 454 is connected to the controller 405. The pressure modulator 454 causes the fluidic state of the water to fluctuate based on a control by the controller 405. The pressure modulator 454 causes the pressure of the water inside the pipe line 20*a* to fluctuate.

A flow regulator 471 is disposed downstream of the pressure modulator 454. The flow regulator 471 regulates the water force (the flow rate). The flow path switching part 472 is disposed downstream of the flow regulator 471. The flow path switching part 472 performs opening and closing and switching of the water supply to the nozzle 473 and/or the nozzle washer 478. The flow regulator 471 and the flow path switching part 472 may be provided as one unit. The flow regulator 471 and the flow path switching part 472 are connected to the controller 405. The operations of the flow regulator 471 and the flow path switching part 472 are controlled by the controller 405.

The nozzle 473, the nozzle washer 478, and a spray nozzle 479 are disposed downstream of the flow path switching part 472. The nozzle 473 receives a drive force from a nozzle motor 476, advances into the bowl 801 of the flush toilet 800, and retracts from the interior of the bowl 801. The nozzle motor 476 is included in a nozzle drive part and causes the nozzle 473 to advance or retreat based on a command from the controller 405.

The nozzle washer 478 washes and removes bacteria from an outer perimeter surface 473*c* (the body) of the nozzle 473 by spraying bacteria-removing water (functional water) from the water discharger 478*a*. The nozzle washer 478 may wash the outer perimeter surface 473*c* of the nozzle 473 by spraying water from the water discharger 478*a*. The spray nozzle 479 sprays the water or functional water into the bowl 801 in mist form. In the example, the spray nozzle 479 is disposed separately from the nozzle 473 for washing the human body. The spraying is not limited thereto; a water discharge port for spraying a mist-like liquid into the bowl 801 may be provided in the nozzle 473.

A bottom wash channel 21, a gentle wash channel 22, and a bidet wash channel 23 also are disposed downstream of the flow path switching part 472. The bottom wash channel 21 and the gentle wash channel 22 guide, toward a bottom wash water discharge port 474*b*, the water supplied from the water supply source 10 or the functional water generated by the electrolytic cell unit 450 via the water transfer part 20. The bidet wash channel 23 guides, toward a bidet wash water discharge port 474*a*, the water supplied from the water supply source 10 or the functional water generated by the electrolytic cell unit 450 via the water transfer part 20.

A surface wash channel 24 and a spray channel 25 also are disposed downstream of the flow path switching part 472. The surface wash channel 24 guides, toward the nozzle washer 478, the water supplied from the water supply source 10 or the functional water generated by the electrolytic cell unit 450 via the water transfer part 20. The spray channel 25 guides, toward the spray nozzle 479, the water supplied from the water supply source 10 or the functional water generated by the electrolytic cell unit 450 via the water transfer part 20.

By controlling the flow path switching part 472, the controller 405 switches the opening and closing of the flow channels of the bottom wash channel 21, the gentle wash channel 22, the bidet wash channel 23, the surface wash channel 24, and the spray channel 25. Thus, the flow path switching part 472 switches between the state of communicating with the pipe line 20*a* and the state of not communicating with the pipe line 20*a* for each of the multiple water discharge ports of the bidet wash water discharge port 474*a*, the bottom wash water discharge port 474*b*, the nozzle washer 478, the spray nozzle 479, etc.

The controller 405 is supplied with power from a power supply circuit 401 and controls the operations of the electromagnetic valve 431, the heat exchanger unit 440, the electrolytic cell unit 450, the pressure modulator 454, the flow regulator 471, the flow path switching part 472, the nozzle motor 476, etc., based on signals from a human body detection sensor 403, the seating detection sensor 404, the flow rate sensor 442, the operation unit 500, etc.

For example, the controller 405 also controls a light-irradiating part 600 based on detection information of the human body detection sensor 403 and/or the seating detection sensor 404. The light-irradiating part 600 irradiates bacteria-removing light, which is light having a bacteria-removing action, simultaneously on the bowl 801 and the periphery of the nozzle 473 (a nozzle storage part 480 described below, etc.). The light-irradiating part 600 is described below.

The human body detection sensor 403 detects the user (the human body) approaching the toilet seat 200. In other words, the human body detection sensor 403 detects the user at the vicinity of the sanitary washing device 100. For example, the controller 405 automatically opens the toilet lid 300 in response to the detection of the user by the human body detection sensor 403.

Various mechanisms (additional functional units) such as a "deodorizing unit", a "room heating unit", a "warm air drying function" that dries the "bottom" or the like of the user sitting on the toilet seat 200 by blowing warm air toward the "bottom" or the like, etc., also may be provided as appropriate in the casing 400. However, according to the invention, such additional functional units may not always be provided.

Figure 3A:
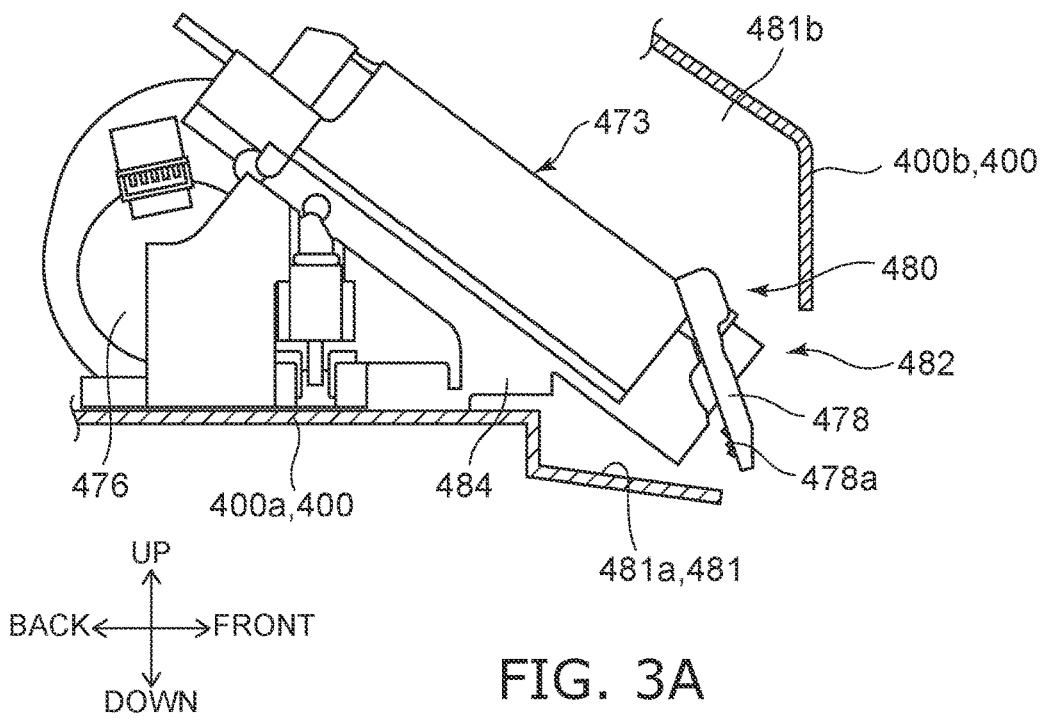
FIGS. 3A and 3B are cross-sectional views illustrating a private part washing nozzle periphery of the toilet device according to the embodiment.
Figure 3B:
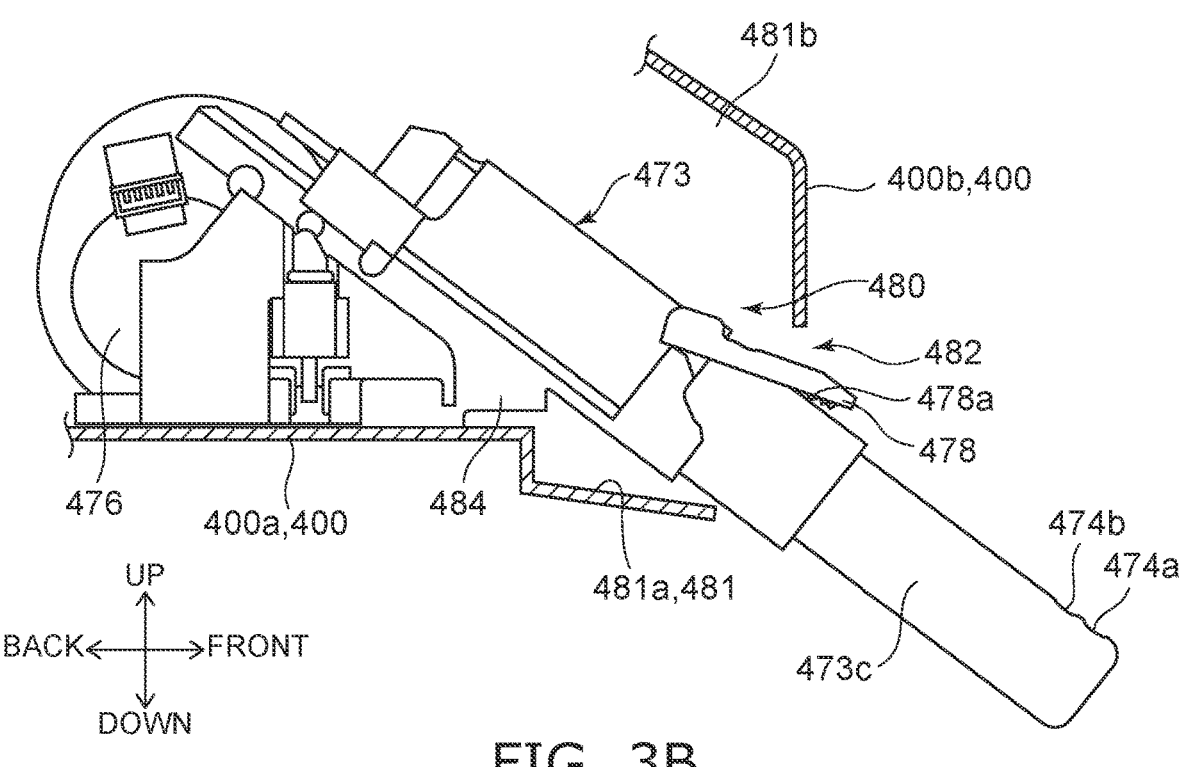

FIGS. 3A and 3B are cross-sectional views illustrating a private part washing nozzle periphery of the toilet device according to the embodiment.

FIG. 3A is a cross-sectional view showing a state in which the nozzle 473 is retracted and stored in the nozzle storage part 480. FIG. 3B is a cross-sectional view showing a state in which the nozzle 473 is advanced.

As illustrated in FIG. 3A, the casing 400 includes the nozzle storage part 480. The nozzle storage part 480 is configured to store the entire nozzle 473 in the state in which the nozzle 473 is retracted. In other words, the nozzle storage part 480 is the part of the interior of the casing 400 in which the nozzle 473 is stored.

The nozzle storage part 480 includes a bottom part 481*a* positioned below the nozzle 473, a sidewall part 481*b* positioned at both the left and right sides of the nozzle 473 (the bottom part 481*a*), and an opening 482 provided in the front end of the nozzle storage part 480. In the example, the bottom part 481*a* is a part of a case plate 400*a* included in the bottom surface of the casing 400. In the example, the sidewall part 481*b* is a part of the case plate 400*a* or a case cover 400*b* included in the side surface of the casing 400. When another component is disposed between the nozzle 473 and the side surface of the casing 400 in the lateral direction (that is, when another component that covers the side of the nozzle 473 is included), the side surface of the component corresponds to the sidewall part 481*b*. An inner wall 481 of the nozzle storage part 480 is formed of the bottom part 481*a* and the sidewall part 481*b*. The top of the nozzle storage part 480 is covered with the case cover 400*b* included in the upper surface of the casing 400. That is, in the example, the case cover 400*b* is included in the upper surface part of the inner wall 481. When another component is disposed between the case cover 400*b* and the nozzle 473 in the vertical direction (that is, when another component that covers the nozzle 473 from above is included), the component corresponds to the upper surface part of the inner wall 481. A nozzle supporter 484 that supports the nozzle 473 to be advanceable and retractable is disposed in the nozzle storage part 480.

The bottom part 481*a* is inclined into the bowl 801 of the flush toilet 800. As a result, the bacteria-removing water that is discharged from the nozzle washer 478, the bidet wash water discharge port 474*a*, and the bottom wash water discharge port 474*b* flows down into the bowl 801 of the flush toilet 800 from the bottom part 481*a*.

The nozzle supporter 484 supports the nozzle 473 below the nozzle 473. The nozzle supporter 484 is inclined downward in a direction from the back toward the front. The nozzle 473 advances and retreats while sliding with respect to the nozzle supporter 484. For example, a tubular member that stores the nozzle 473 may be included in the nozzle storage part 480. In such a case, the part of the tubular member positioned below the nozzle 473 corresponds to the bottom part 481*a*; the part of the tubular member positioned at the side of the nozzle 473 corresponds to the sidewall part 481*b*; and the part of the tubular member positioned above the nozzle 473 corresponds to the upper surface part.

The nozzle washer 478 is disposed at the tip of the nozzle 473 when the nozzle 473 is retracted into the casing 400. The nozzle washer 478 includes the water discharger 478*a* in which a water discharge hole that discharges water and bacteria-removing water toward the outer perimeter surface 473*c* of the nozzle 473 is formed. The opening 482 is provided in the front end of the nozzle storage part 480. The opening 482 is disposed at the lower side of the front surface of the casing 400. The nozzle washer 478 is positioned behind the opening 482. For example, the nozzle washer 478 washes the outer perimeter surface 473*c* (the body) of the nozzle 473 by spraying water and/or bacteria-removing water from the water discharger 478*a* when the nozzle 473 advances and retreats.

The nozzle 473 is stored in the nozzle storage part 480 as illustrated in FIG. 3A when not in use. When the nozzle 473 performs a private part wash, the nozzle 473 slides frontward and downward with respect to the nozzle storage part 480 as illustrated in FIG. 3B. For example, the nozzle 473 is washed by the water discharged from the nozzle washer 478 until the nozzle 473 reaches a prescribed position.

When the nozzle 473 reaches the prescribed position, the private part of the user is washed by discharging water toward the private part from the bidet wash water discharge port 474*a* or the bottom wash water discharge port 474*b*. When the private part wash is completed, the nozzle 473 slides backward and upward toward the nozzle storage part 480. For example, the nozzle 473 is washed by water discharged from the water discharger 478*a* until the nozzle 473 is stored in the nozzle storage part 480. The nozzle 473 retreats to a prescribed position and is stored in the nozzle storage part 480.

At this time, the water (the bacteria-removing water) discharged from the water discharger 478*a* flows through the interior of the nozzle storage part 480 and almost completely flows down into the bowl 801 of the flush toilet 800 from the opening 482. However, there are cases where the bacteria-removing water remains at the inner wall 481 of the nozzle storage part 480 due to, for example, the shape of the nozzle storage part 480, surface tension of the bacteria-removing water, etc. The concentration of the bacteria-removing components in the remaining water attenuates over time. Therefore, the interior of the nozzle storage part 480 undesirably becomes an environment in which bacteria and/or mold easily occur.

Figure 4A:
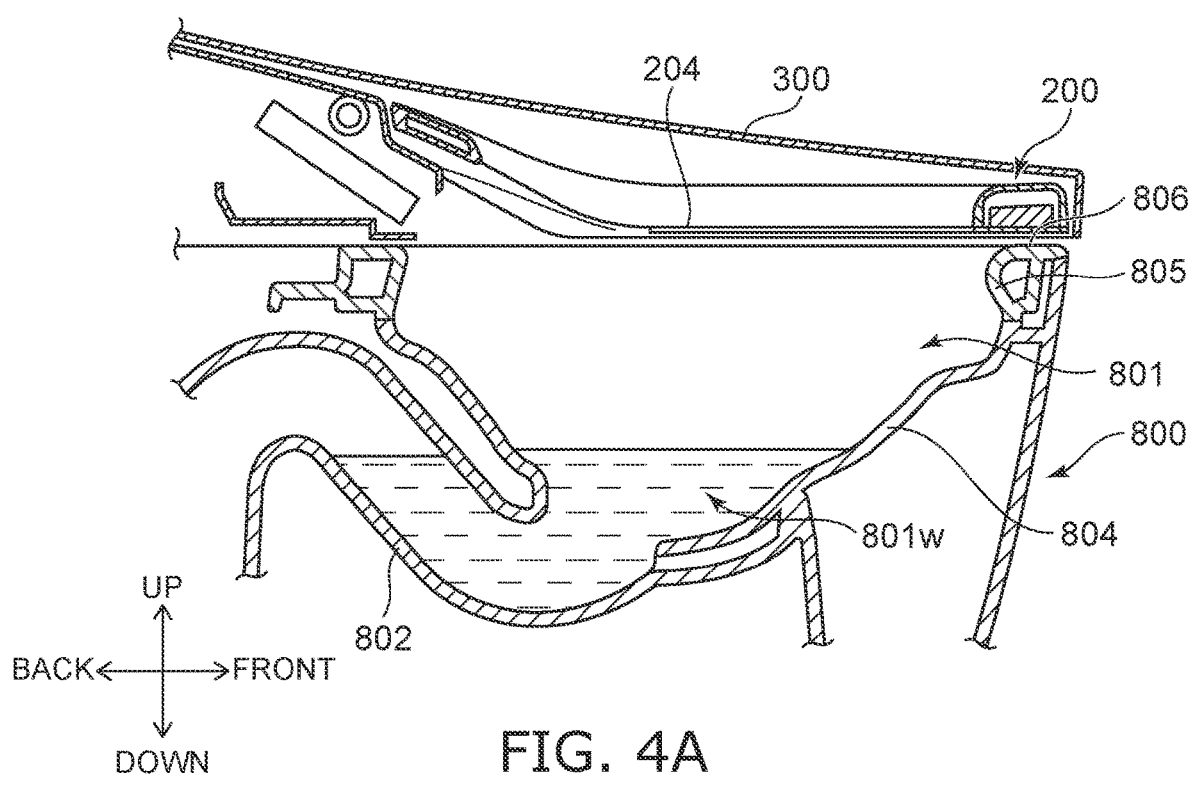
FIGS. 4A and 4B are cross-sectional views illustrating the toilet device according to the embodiment.
Figure 4B:
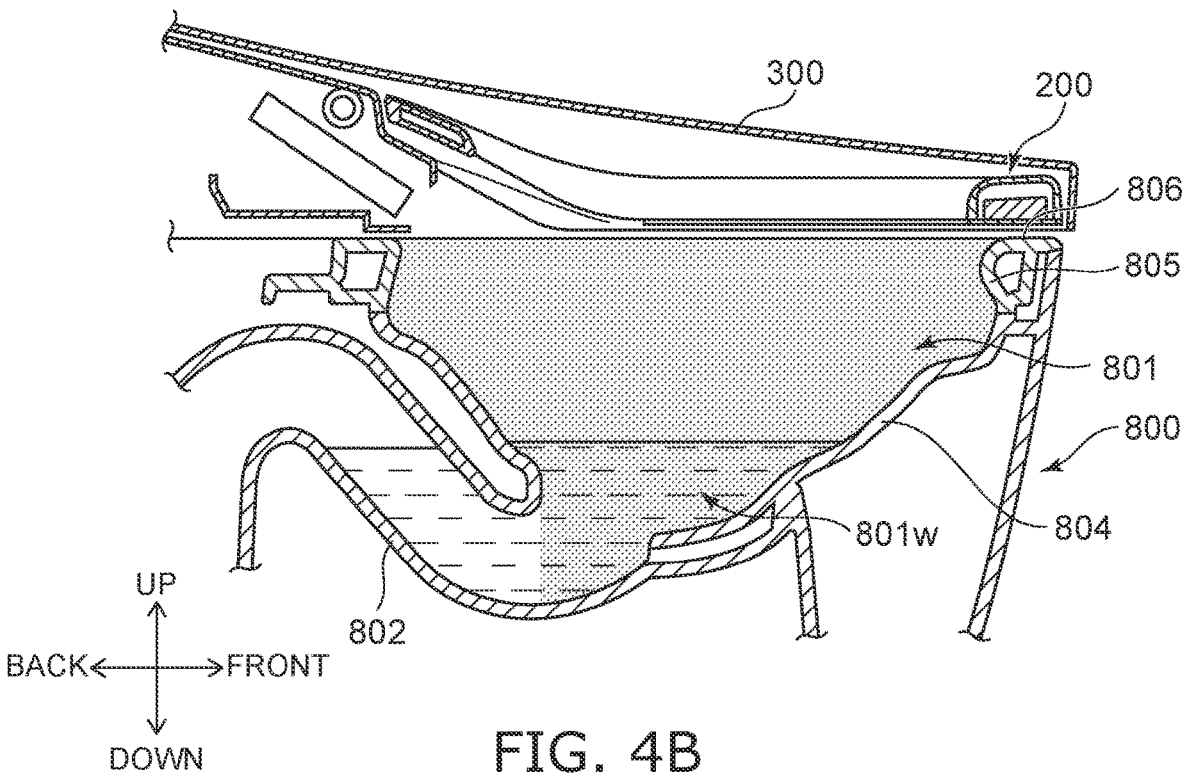

FIGS. 4A and 4B are cross-sectional views illustrating the toilet device according to the embodiment.

Figure 5A:
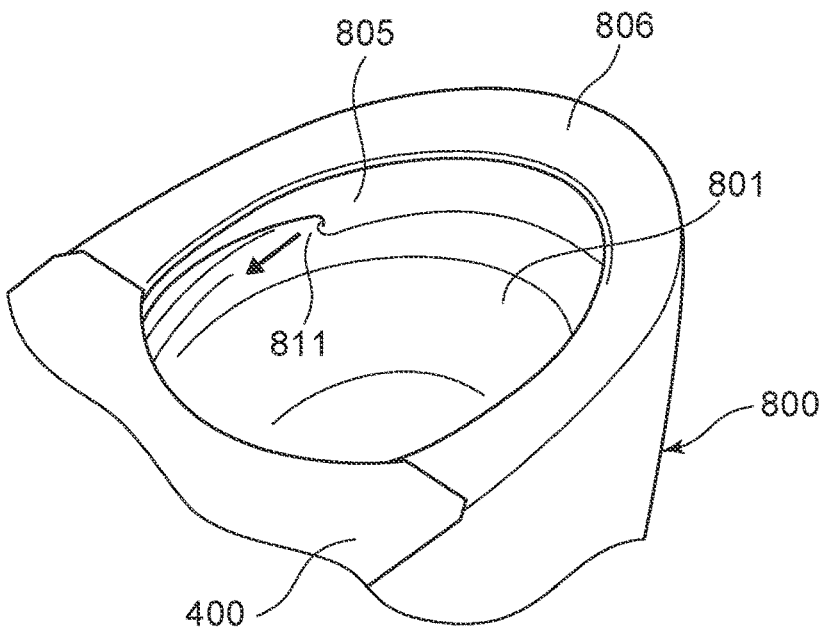
FIGS. 5A and 5B are a perspective view and a plan view illustrating the flush toilet of the toilet device according to the embodiment.
Figure 5B:
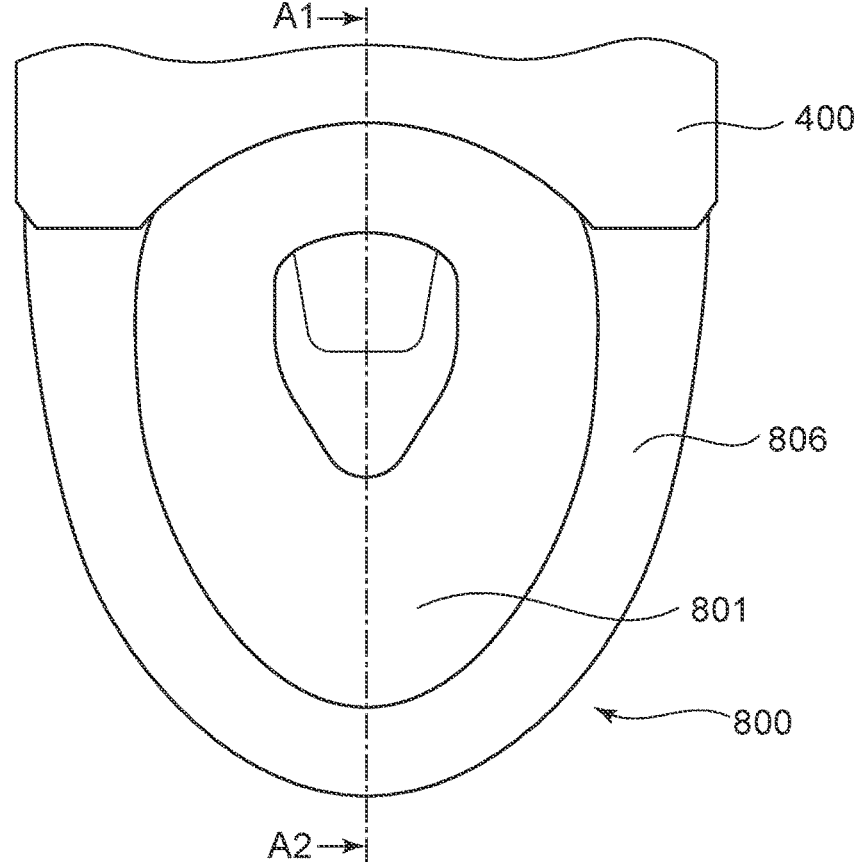

FIGS. 5A and 5B are a perspective view and a plan view illustrating the flush toilet of the toilet device according to the embodiment.

FIGS. 4A and 4B are cross-sectional views at the position of line A1-A2 shown in FIG. 5B.

As shown in FIG. 4A, the flush toilet 800 includes the concave bowl 801 that receives human waste, and a drain part 802 that drains the human waste together with water. The bowl 801 includes a receiving part 804, and a rim part 805 disposed on the receiving part 804. The rim part 805 is a ring-shaped part forming the upper edge part of the flush toilet 800. The rim part 805 includes an upper surface 806. The upper surface 806 faces a back surface 204 of the closed toilet seat 200. The bowl 801 corresponds to the cross-hatched part in FIG. 4B. Standing water 801*w* collects inside the bowl 801.

FIG. 5A is a perspective view illustrating the flush toilet 800; and FIG. 5B is a plan view illustrating the flush toilet 800. The flush toilet 800 includes a water discharge port 811 provided in the rim part 805. The water discharge port 811 discharges wash water into the bowl 801 to discharge human waste (e.g., excrement of the user, etc.) from the interior of the bowl 801.

Toilet flushing in which wash water is supplied from the water discharge port 811 into the bowl 801 is performed when, for example, the user uses a switch disposed in the operation unit (the remote control) 500 or the like to perform the toilet flushing operation, or the user stands up from the toilet seat 200. As a result, the human waste inside the bowl 801 is drained into the drain part 802; and the surface of the bowl 801 is washed. Thus, the organic substances included in the human waste easily adhere to the bowl 801 due to the contact of the human waste with the bowl 801. Therefore, the bowl 801 is a location at which stains are easily generated by the proliferation of bacteria feeding on the organic substances.

Other than the bacteria-removing water described above, techniques to suppress bacterial growth include the use of ions, ozone, and the like. Although ions, ozone, and the like are techniques that aim to affect the stain suppression part by means of airflow, it is difficult to control the effective area of the airflow; and uncontrolled airflow may cause discrepancies such as functional failure due to corrosion of electronic components and the like inside the case, degradation of resin materials, etc. On the other hand, it is possible to irradiate light only on the stain suppression part. Discrepancies due to the degradation of the resin materials can be avoided by appropriately controlling the irradiation amount according to the wavelength and irradiation object materials.

Although ultraviolet is used to sterilize the interior of the nozzle storage part in conventional art, the problem of being unable to sterilize the inner surface of the bowl is addressed by 2020-186531 JP A, in which ultraviolet can be irradiated on both the nozzle storage part and the bowl by a common light-irradiating part by moving the light-irradiating part irradiating ultraviolet between the nozzle storage part and the bowl. Thus, according to 2020-186531 JP A, the cost of increasing the light-irradiating parts is reduced by utilizing the common light-irradiating part 600.

However, 2020-186531 JP A is problematic in that it takes time for the irradiation sequence to complete because the common light-irradiating part irradiates the ultraviolet sequentially on the nozzle storage part and the bowl. Bacteria proliferate by division, and therefore proliferate by a power of two over time. That is, when the irradiation is slow, the bacteria count (the initial bacteria count) that must be killed increases by a power of two with respect to the elapsed time. Because the bacteria count must be maintained at or below a prescribed value to suppress visible stains, the integrated irradiance necessary to keep the bacteria count at or below the prescribed value also increases as the initial bacteria count increases. By starting the irradiation of the light as soon as possible after the bacteria adheres, a lower integrated irradiance can be used to reduce the bacteria count to the prescribed value or less (or maintain the bacteria count at or below the prescribed value) to suppress the visible stains.

Therefore, according to the embodiment, the common light-irradiating part 600 irradiates the bacteria-removing light simultaneously on the nozzle storage part 480 and the bowl 801.

Figure 6:
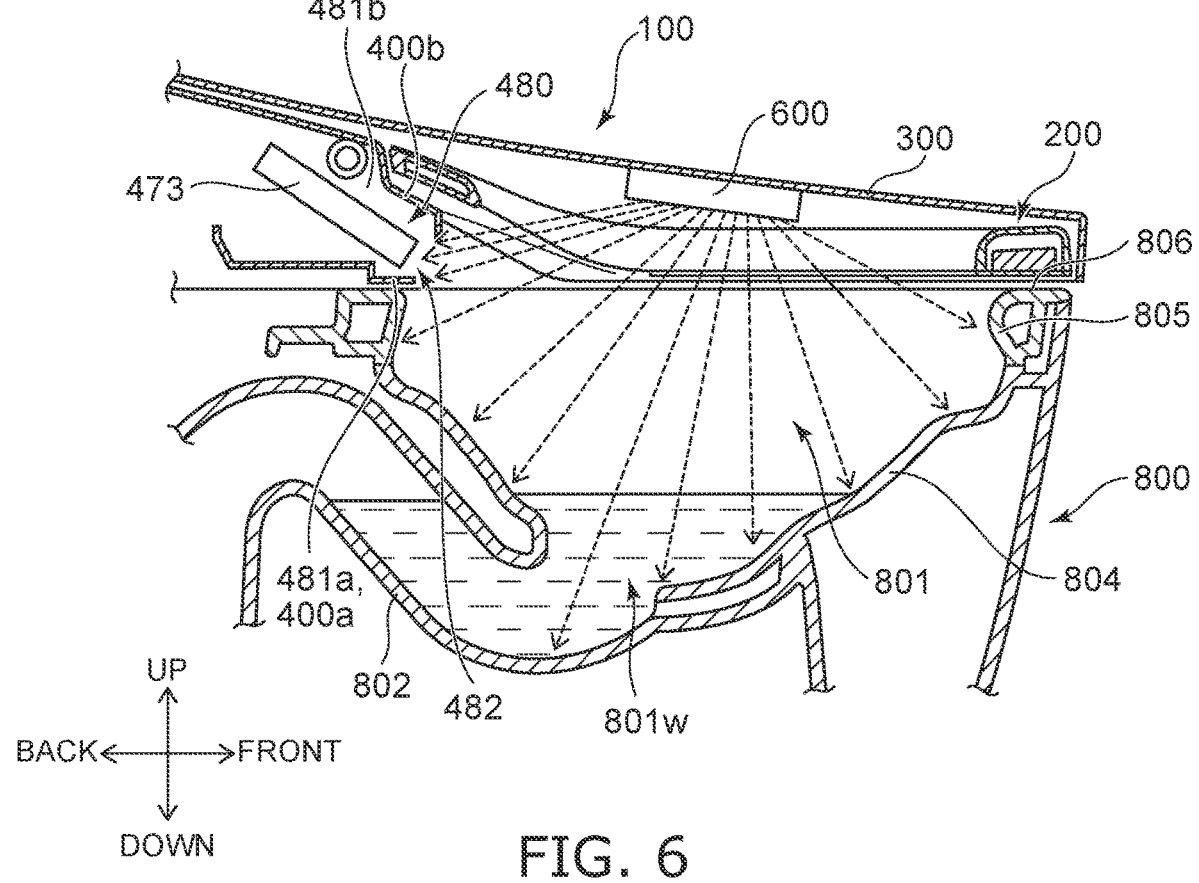
FIG. 6 is a cross-sectional view illustrating an example of the toilet device according to the embodiment.

FIG. 6 is a cross-sectional view illustrating an example of the toilet device according to the embodiment.

FIG. 6 is a cross-sectional view at the position of line A1-A2 shown in FIG. 5B.

As illustrated in FIG. 6, the sanitary washing device 100 includes the light-irradiating part 600 that irradiates bacteria-removing light, which is light having a bacteria-removing action. The bacteria-removing action is, for example, an action of suppressing bacterial growth.

By irradiating the bacteria-removing light, at least a part of the bacteria adhered to the object can be annihilated or inactivated; and bacterial growth can be suppressed (removed). The wavelength of the bacteria-removing light is 250 nm to 480 nm. For example, it is favorable for the bacteria-removing light to include ultraviolet. Results of investigations by the inventors show that the irradiation of light of a wavelength of the 250 nm to 300 nm vicinity can reprogram the DNA of bacteria, mold, etc., so that the bacteria, mold, etc., are inactivated and cannot proliferate. It is also found that the irradiation of light of a wavelength of 300 to 480 nm vicinity acts on moisture inside the body of bacteria, mold, etc., which generates reactive oxygen that annihilates or inactivates the bacteria. The inventors have confirmed that hydrogen peroxide is generated in tap water by irradiating light of a wavelength of 365 nm on tap water. This means that hydrogen peroxide is generated in water when producing radicals. The inventors also confirmed that bacteria in water can be removed by irradiating light of a wavelength of 300 nm to 480 nm on the bacteria in water. In the example, the light-irradiating part 600 is disposed at the back surface of the toilet lid 300.

The light-irradiating part 600 includes, for example, at least one light-emitting part (light-emitting body). One or multiple light-emitting parts may be included in the light-irradiating part 600. The light-emitting part is, for example, an LED (Light-Emitting Diode). The light-emitting part is not limited to an LED and may be, for example, a LD (Laser Diode), an OLED (Organic Light-Emitting Diode), etc. A cold cathode fluorescent tube or a hot cathode fluorescent tube may be used instead of a light-emitting element. For example, the light-emitting part is connected to the controller 405 shown in FIG. 2 via a substrate, and is lit and unlit based on a control of the controller 405. The controller 405 controls the operation of the light-irradiating part 600 by controlling the light-emitting part to be lit or unlit. For example, the controller 405 also may control the total luminous flux of the light-emitting part by regulating the voltage applied to the light-emitting part.

In FIG. 6, the light-irradiating part 600 irradiates bacteria-removing light having a bacteria-removing action toward the nozzle storage part 480 and the bowl 801. Bacterial growth at the nozzle storage part 480 and the bowl 801 is suppressed by the irradiation of the bacteria-removing light. The occurrence of stains at the nozzle storage part 480 and the bowl 801 also is suppressed thereby. The light-irradiating part 600 irradiates the bacteria-removing light on at least a part of the nozzle storage part 480 and at least a part of the bowl 801. The light-irradiating part 600 may irradiate the bacteria-removing light on the entire nozzle storage part 480. The light-irradiating part 600 may irradiate the bacteria-removing light on the entire bowl 801.

For example, when the light-emitting part is a sterilizing lamp (that is, when the bacteria-removing light is sterilizing rays), the minimum integrated irradiance necessary to suppress growth of bacteria that may be present in the toilet device 1 is 5 mJ/cm$^2$. The sterilizing rays are ultraviolet having a wavelength at the 260 nm vicinity. By setting the bacteria-removing light irradiated from the light-emitting part on the nozzle storage part 480 and the bowl 801 to have an integrated irradiance of not less than 5 mJ/cm$^2$, bacterial growth can be suppressed, and the occurrence of stains can be suppressed.

As illustrated in FIG. 6, a cost increase can be prevented by irradiating the bacteria-removing light on the nozzle storage part 480 and the bowl 801 from the common light-irradiating part 600. By irradiating the bacteria-removing light simultaneously on the nozzle storage part 480 and the bowl 801, the irradiation of the bacteria-removing light can be started when the bacteria count adhered to the nozzle storage part 480 and the bowl 801 is as low as possible. Therefore, the integrated irradiance necessary to suppress bacterial growth can be reduced. For the same irradiance, the prescribed integrated irradiance can be reached by a shorter irradiation period and bacterial growth can be suppressed better when the irradiation is started simultaneously than when the irradiation is performed sequentially. Accordingly, bacterial growth at the nozzle storage part 480 and the bowl 801 can be suppressed by irradiating bacteria-removing light for a short period of time while preventing a cost increase due to an increase of the light-irradiating parts 600. As a result, the occurrence of stains can be suppressed, and a hygienic sanitary washing device 100 (toilet device 1) can be provided.

As described above, when the bacteria-removing light is sterilizing rays, the integrated irradiance necessary for bacterial growth suppression is not less than 5 mJ/cm$^2$. Because the integrated irradiance is the product of the irradiance and the irradiation time, an irradiance of not less than 1 µW/cm$^2$ is necessary to suppress bacterial growth for, for example, 1.4 hours. For example, the irradiance can be measured using the UV power meter C9536/H9535 (Hamamatsu Photonics K. K.) when the wavelength of the bacteria-removing light is within the range of 250 to 300 nm, the UV power meter C9536/H9958 (Hamamatsu Photonics K. K.) when the wavelength of the bacteria-removing light is within the range of 300 to 410 nm, and the ACCU-CAL™ 50-LED UV radiometer (Dymax Corporation) when the wavelength of the bacteria-removing light is in the range of 350 to 450 nm. For example, the irradiance can be measured by a method conforming to JIS Z 8000-7:2022.

It is favorable for the average value of the irradiance of the inner surface of the nozzle storage part 480 irradiated with the bacteria-removing light to be greater than the average value of the irradiance of the surface of the bowl 801 irradiated with the bacteria-removing light.

The inner surface of the nozzle storage part 480 is the surface of the inner wall 481 of the nozzle storage part 480. When an openable and closable nozzle lid 483 (see FIG. 9) is disposed at the opening 482 of the nozzle storage part 480, the nozzle lid 483 forms a part of the nozzle storage part 480. In such a case, the back surface (the surface at the back side) of the nozzle lid 483 also is included in the inner surface of the nozzle storage part 480. As described above, the surface of the bowl 801 refers to the surface of the cross-hatched part shown in FIG. 4B.

The average value of the irradiance is obtained by dividing the calculation surface (the inner surface of the nozzle storage part 480 or the surface of the bowl 801) into a prescribed section area (e.g., 1 mm×1 mm sections), by measuring and calculating the value of the irradiated irradiance per section area, and by dividing the total of the measured irradiance by the number of sections. For example, a measurement device such as the UV power meter C9536/H9958 (Hamamatsu Photonics K. K.) may be used to measure the illuminance per prescribed section area.

Among the irradiation objects of the bacteria-removing light, the nozzle storage part 480 is inside the casing 400; and the bowl 801 is outside the casing 400. The bowl 801 is washed each time the user uses the toilet device 1 (the flush toilet 800). On the other hand, for example, the nozzle 473 and the nozzle storage part 480 are not washed when a male urinates standing up because the nozzle 473 is not used. That is, the bacteria count at the bowl 801 is easily reduced because the bacteria is rinsed away by washing each time the toilet device 1 is used. In contrast, it is difficult to reduce the bacteria count at the nozzle storage part 480 because there are cases where the nozzle storage part 480 is not washed even when the toilet device 1 is used. Therefore, there are cases where the nozzle storage part 480 has a greater bacteria count than the bowl 801. The integrated irradiance necessary to suppress bacterial growth increases as the bacteria count increases. Therefore, by setting the average value of the irradiance of the inner surface of the nozzle storage part 480 irradiated with the bacteria-removing light to be greater than the average value of the irradiance of the surface of the bowl 801 irradiated with the bacteria-removing light, the bacteria removal intensity at the nozzle storage part 480, which tends to have a greater bacteria count than the bowl 801, can be set to be greater than the bacteria removal intensity at the bowl 801. Accordingly, bacterial growth at the nozzle storage part 480 and the bowl 801 can be efficiently suppressed. The occurrence of stains at the nozzle storage part 480 and the bowl 801 can be efficiently suppressed thereby.

It is favorable for the average value of the irradiance of the inner surface of the nozzle storage part 480 irradiated with the bacteria-removing light to be, for example, not less than 4 µW/cm$^2$ and not more than 100 mW/cm$^2$. It is favorable for the average value of the irradiance of the surface of the bowl 801 irradiated with the bacteria-removing light to be, for example, not less than 1 µW/cm$^2$ and not more than 25 mW/cm$^2$.

Figure 7:
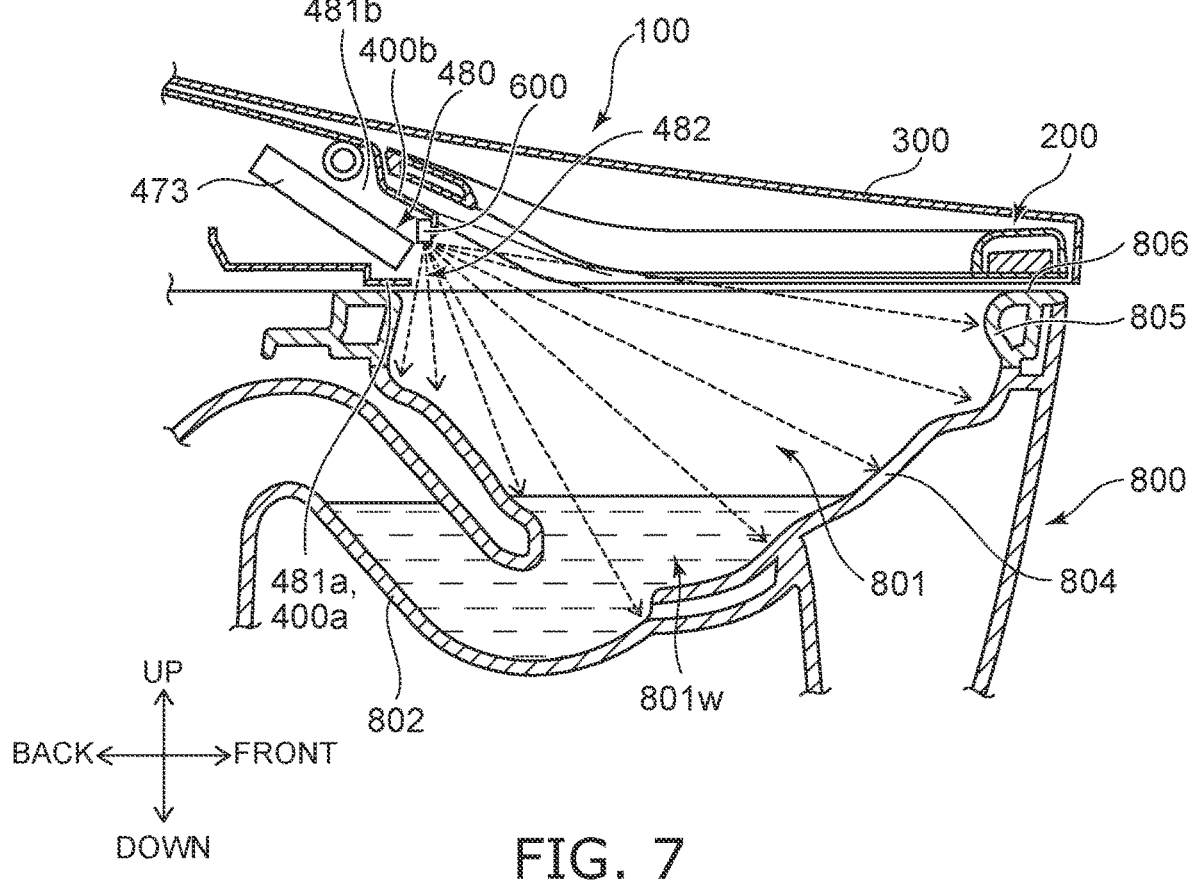
FIG. 7 is a cross-sectional view illustrating an example of the toilet device according to the embodiment.

FIG. 7 is a cross-sectional view illustrating an example of the toilet device according to the embodiment.

FIG. 7 is a cross-sectional view at the position of line A1-A2 shown in FIG. 5B.

As illustrated in FIG. 7, it is desirable for the common light-irradiating part 600 irradiating the bacteria-removing light on the nozzle storage part 480 and the bowl 801 to be disposed inside the casing 400.

As described above, compared with the bowl 801, the nozzle storage part 480 is washed less frequently and may have a greater bacteria count. The integrated irradiance necessary to suppress bacterial growth increases as the bacteria count increases. Generally, for light sources other than lasers, the irradiance radiated from the light source increases as the distance decreases. By disposing the light-irradiating part 600 inside the casing 400, the bacteria-removing light can be irradiated on the nozzle storage part 480 with a larger irradiance than the bowl 801. Therefore, by disposing the light-irradiating part 600 inside the casing 400, even when the bacteria-removing light is irradiated from the common light-irradiating part 600 simultaneously on the bowl 801 and the nozzle storage part 480, which tends to have a greater bacteria count than the bowl 801, the irradiation time of the bacteria-removing light can be reduced because the difference between the time to reduce the bacteria count of the nozzle storage part 480 to or below the prescribed value and the time to reduce the bacteria count of the bowl 801 to or below the prescribed value can be reduced.

When the light-irradiating part 600 is disposed inside the casing 400 and used to irradiate the bacteria-removing light on the nozzle storage part 480 and the bowl 801, it is favorable to irradiate the bacteria-removing light on the bowl 801 via the opening 482 provided in the front end of the nozzle storage part 480. The opening 482 is, for example, the part surrounded with the bottom part 481a, the sidewall part 481b, and the case cover 400b. The light-irradiating part 600 may be disposed inside the casing 400 and may be used to irradiate the bacteria-removing light on the bowl 801 via an opening provided in the bottom part 481a. In such a case, the opening that is provided in the bottom part 481a may be filled with a transparent member; and the bacteria-removing light may be irradiated on the bowl 801 via the transparent member. When the nozzle lid 483 that is configured to open and close the opening 482 is included (see FIG. 9), the light-irradiating part 600 may be disposed inside the casing 400; and the bacteria-removing light may be irradiated on the bowl 801 through a gap between the bottom part 481*a* and the nozzle lid 483.

It is desirable for the average value of the irradiance of the surface of a bowl back part 801*b* irradiated with the bacteria-removing light to be greater than the average value of the irradiance of the surface of a bowl front part 801*a* irradiated with the bacteria-removing light.

Figure 8A:
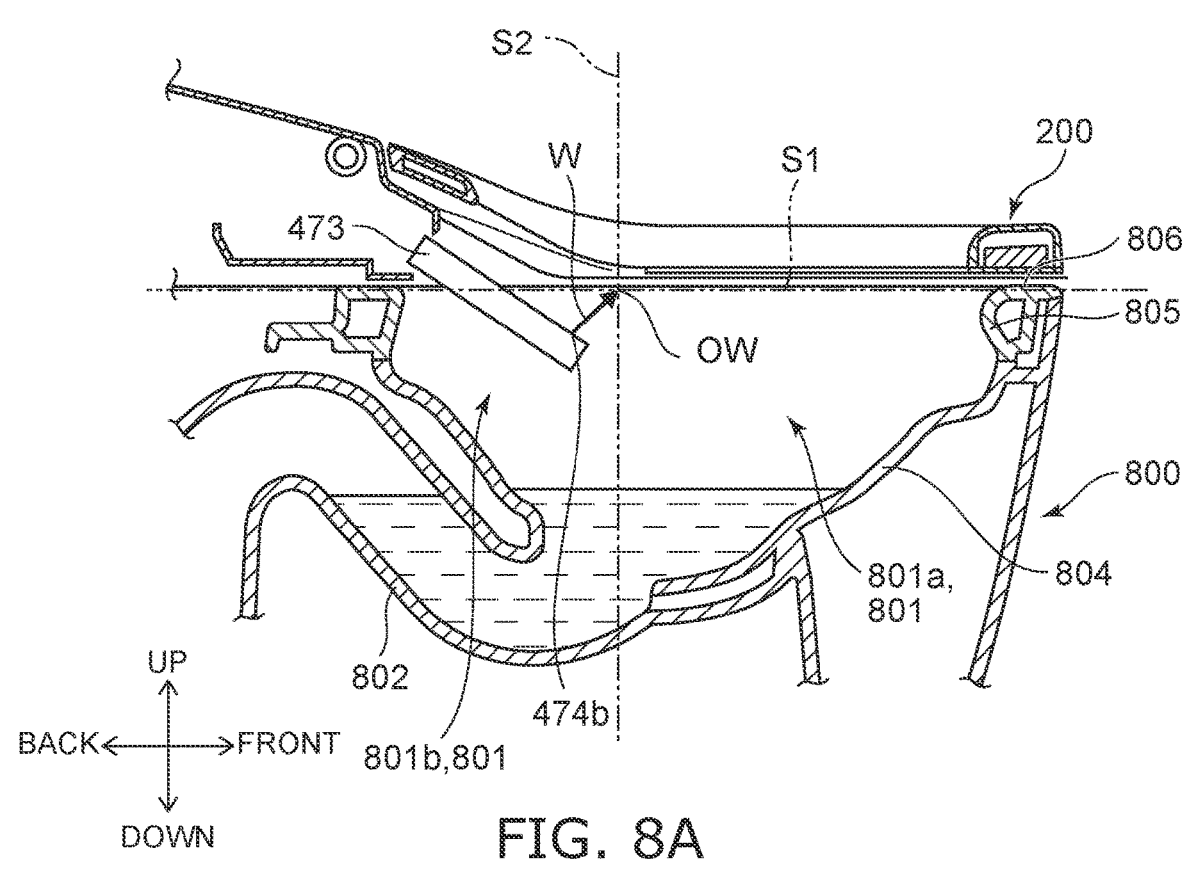
FIGS. 8A and 8B are explanatory drawings of the bowl front part and bowl back part of the toilet device according to the embodiment.
Figure 8B:
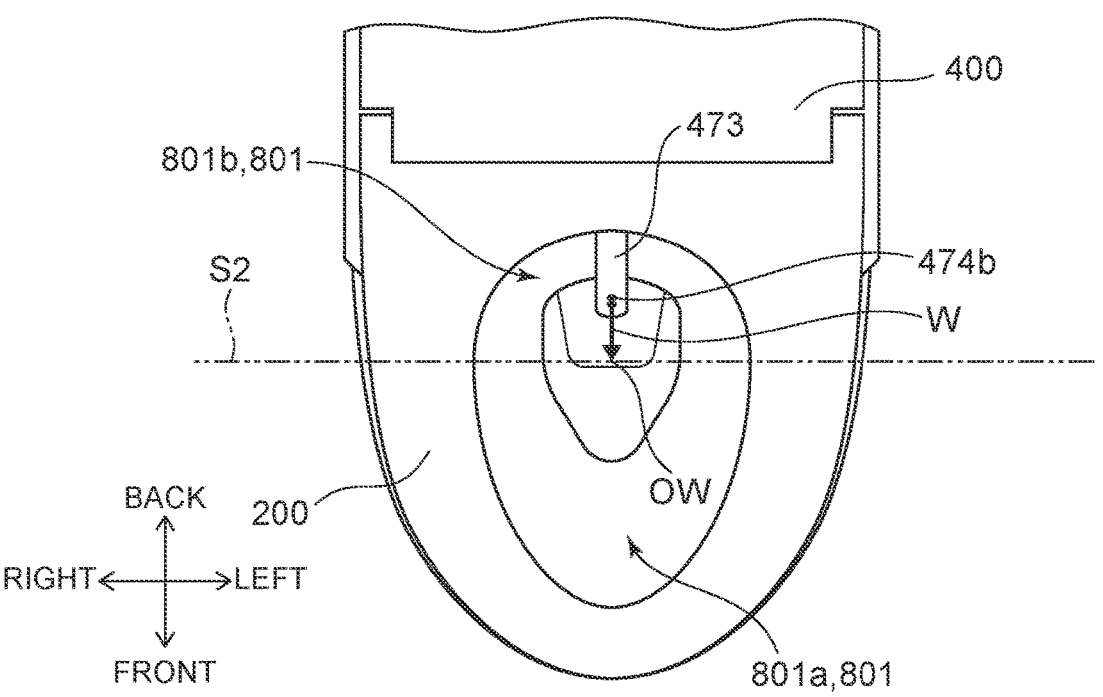

FIGS. 8A and 8B are explanatory drawings of the bowl front part and bowl back part of the toilet device according to the embodiment.

FIG. 8A is a cross-sectional view at the position of line A1-A2 shown in FIG. 5B.

As illustrated in FIGS. 8A and 8B, when referenced to an anus washing position OW, the bowl 801 is divided into a bowl front part 801*a* and a bowl back part 801*b*. The anus washing position OW is the point at which an extension plane S1 of the upper surface 806 of the rim part 805 crosses a straight line along a discharge direction of water W discharged from the bottom wash water discharge port 474*b* when the nozzle 473 is advanced to the maximum length. The anus washing position OW is the general anus position when the user is seated on the toilet seat 200. FIGS. 8A and 8B show a vertical plane S2 that is orthogonal to the extension plane S1 at the anus washing position OW. The bowl front part 801*a* is the part of the bowl 801 positioned frontward of the vertical plane S2 (the anus washing position OW). The bowl back part 801*b* is the part of the bowl 801 positioned behind the vertical plane S2 (the anus washing position OW).

The user that is seated on the toilet seat 200 defecates in a forward-tilted posture. Therefore, the organic substances included in the feces are likely to adhere to the bowl back part 801*b* positioned behind the anus washing position OW. In other words, the bowl back part 801*b* has a greater initial bacteria count than the bowl front part 801*a* because organic substances, which nourish bacteria and create an environment favorable for bacterial growth, tend to adhere to the bowl back part 801*b*. As described above, the integrated irradiance necessary to reduce the bacteria count to or below the prescribed value also increases as the initial bacteria count increases. Therefore, by setting the average value of the irradiance of the surface of the bowl back part 801*b* irradiated with the bacteria-removing light to be greater than the average value of the irradiance of the surface of the bowl front part 801*a* irradiated with the bacteria-removing light, the bacteria removal intensity at the bowl back part 801*b*, which tends to have a greater initial bacteria count than the bowl front part 801*a*, can be set to be greater than the bacteria removal intensity at the bowl front part 801*a*. Accordingly, the bacterial growth at the bowl front part 801*a* and the bowl back part 801*b* can be efficiently suppressed. As a result, the difference can be small between the time to reduce the bacteria count at the bowl back part 801*b* to or below the prescribed value and the time to reduce the bacteria count at the bowl front part 801*a* to or below the prescribed value even when the bacteria-removing light is irradiated from the common light-irradiating part 600 simultaneously on the bowl front part 801*a* and the bowl back part 801*b*, which tends to have a greater initial bacteria count than the bowl front part 801*a*; therefore, the irradiation time of the bacteria-removing light can be reduced, and the occurrence of stains at the bowl 801 can be efficiently suppressed.

The specific configurations of the nozzle storage part 480 and the light-irradiating part 600 are modifiable as appropriate.

Figure 9:
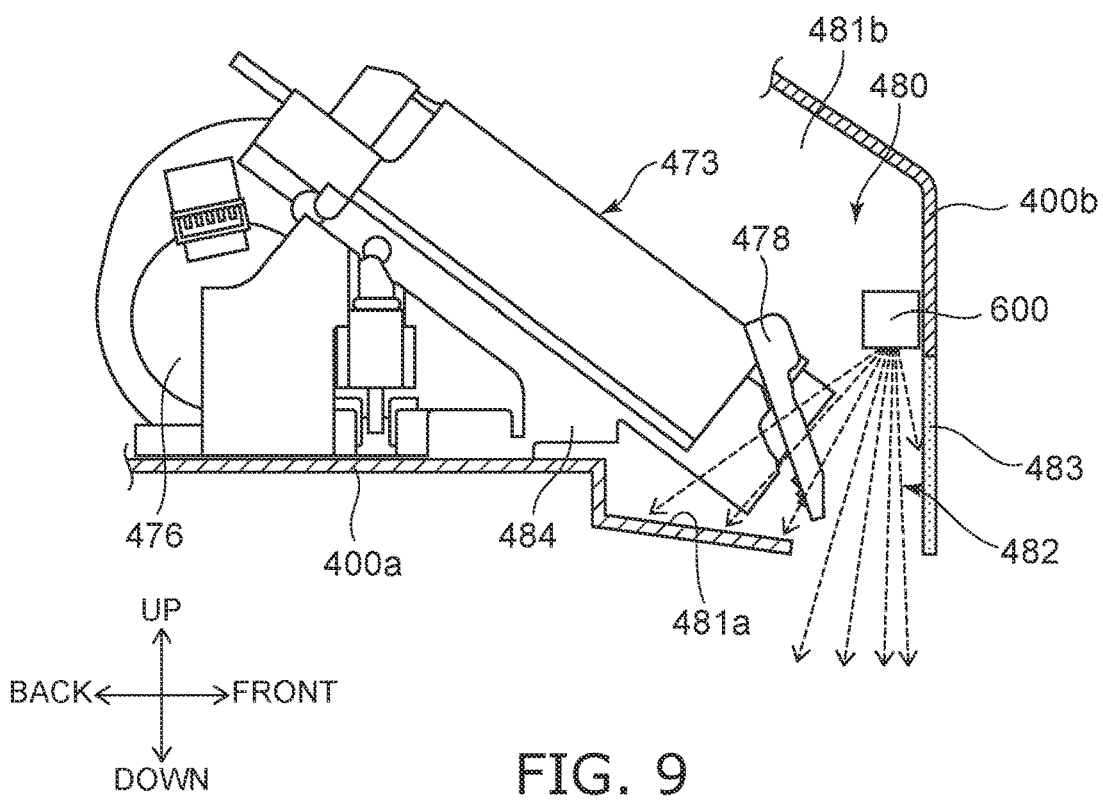
FIG. 9 is a cross-sectional view illustrating an example of the private part washing nozzle periphery of the toilet device according to the embodiment.

FIG. 9 is a cross-sectional view illustrating an example of the private part washing nozzle periphery of the toilet device according to the embodiment.

As illustrated in FIG. 9, the nozzle lid 483 that is configured to open and close the opening 482 of the nozzle storage part 480 may be disposed in the nozzle storage part 480. For example, the nozzle lid 483 is in an open state when advancing the nozzle 473, and in a closed state when retracting the nozzle 473. The light-irradiating part 600 may be mounted inside the casing 400, and may be disposed higher than the front end of the nozzle 473. By disposing the light-irradiating part 600 higher than the front end of the nozzle 473 inside the casing 400, the bacteria-removing light can be irradiated also on the back surface (the surface at the back side) of the nozzle lid 483; and the bacteria-removing light can be efficiently irradiated on the nozzle storage part 480 and the bowl 801.

Figure 10:
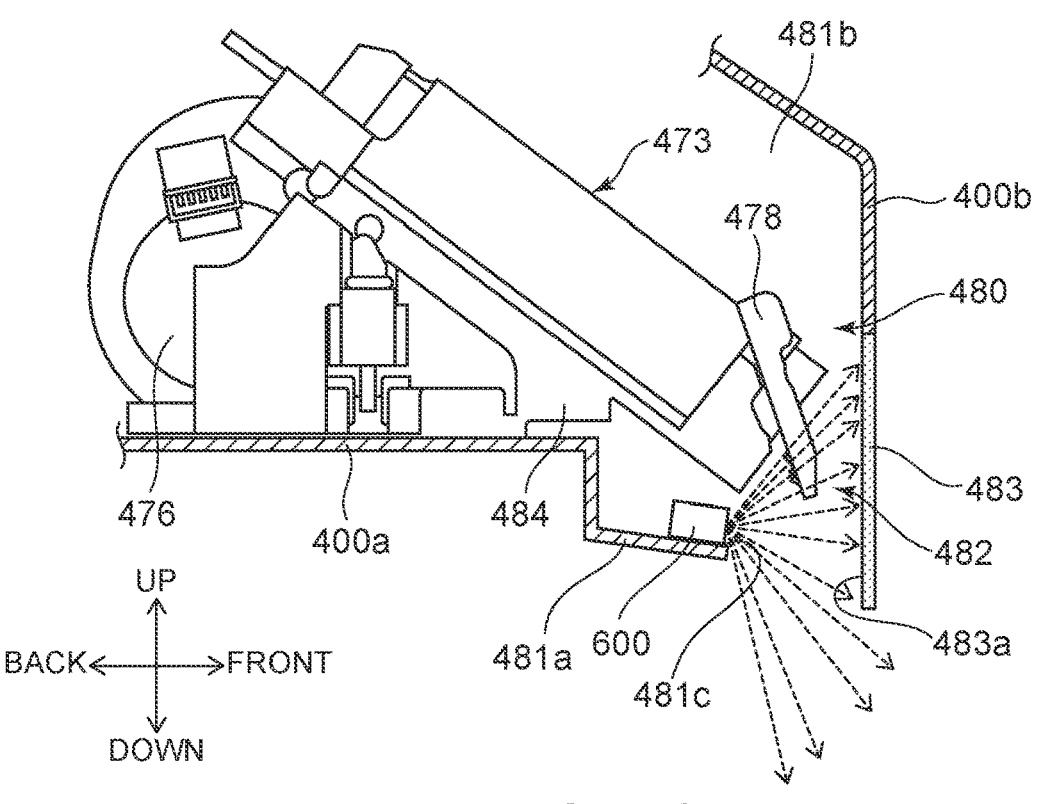
FIG. 10 is a cross-sectional view illustrating an example of the private part washing nozzle periphery of the toilet device according to the embodiment.

FIG. 10 is a cross-sectional view illustrating an example of the private part washing nozzle periphery of the toilet device according to the embodiment.

As illustrated in FIG. 10, the nozzle lid 483 that is configured to open and close the opening 482 of the nozzle storage part 480 may be disposed in the nozzle storage part 480. The light-irradiating part 600 may be mounted inside the casing 400, and may be disposed between the nozzle 473 and the bottom part 481*a* of the nozzle storage part 480. Locations at which stains tend to occur are, for example, locations at which water tends to remain. Examples of locations at which water tends to remain include, for example, the bottom part 481*a* of the nozzle storage part 480 to which water droplets run down and collect, an end part 481*c* of the nozzle storage part 480 and a back surface lower part 483*a* of the nozzle lid 483 at which water tends to stay due to surface tension, etc. By mounting the light-irradiating part 600 between the nozzle 473 and the bottom part 481*a*, the bacteria-removing light can be efficiently irradiated on locations at which water tends to remain and stains tend to occur.

Figure 11A:
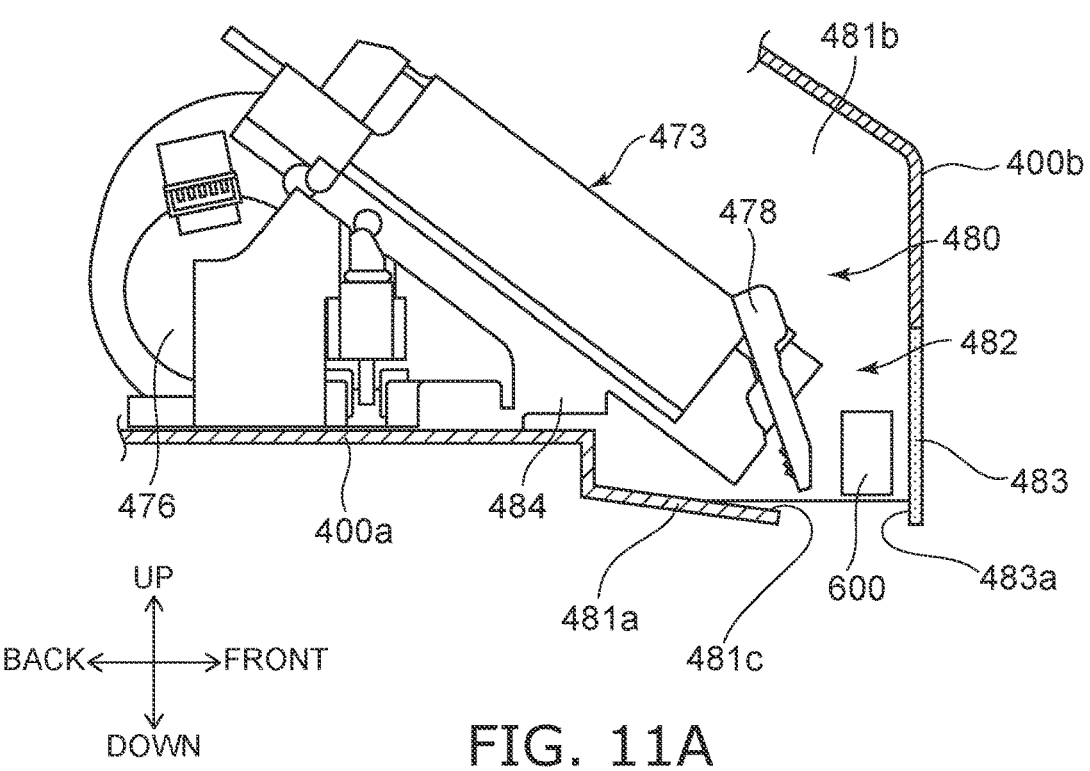
FIGS. 11A and 11B are a cross-sectional view and a front view illustrating an example of the private part washing nozzle periphery of the toilet device according to the embodiment.
Figure 11B:
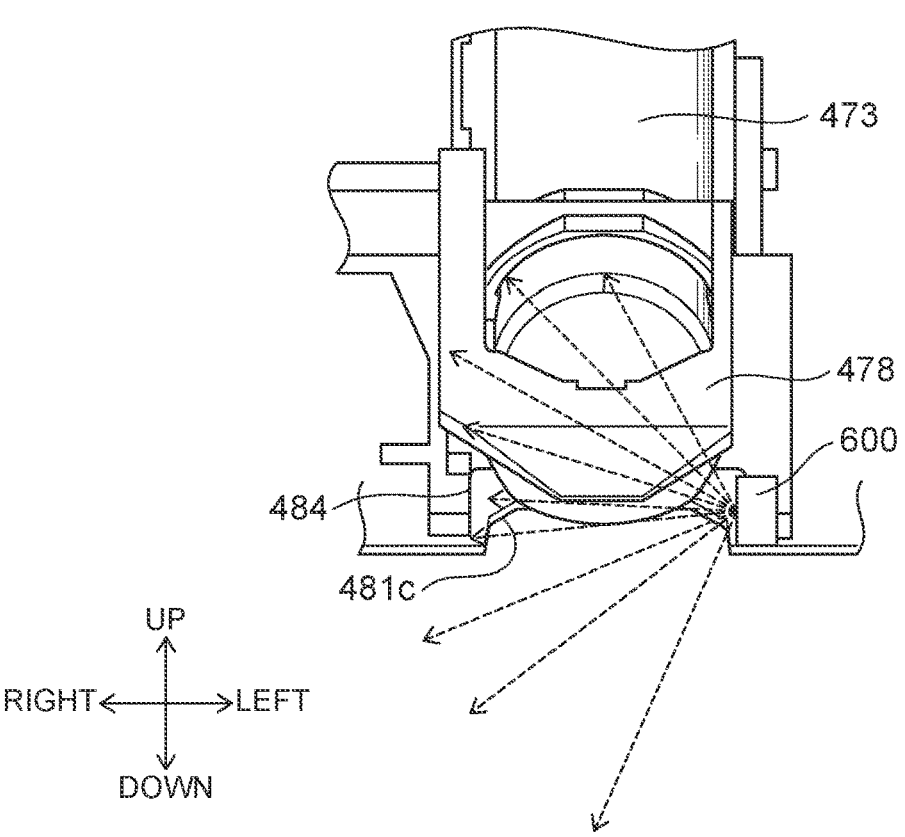

FIGS. 11A and 11B are a cross-sectional view and a front view illustrating an example of the private part washing nozzle periphery of the toilet device according to the embodiment.

FIG. 11B shows a state in which the case cover 400*b* and the nozzle lid 483 are removed.

As illustrated in FIGS. 11A and 11B, the nozzle lid 483 that is configured to open and close the opening 482 of the nozzle storage part 480 may be disposed in the nozzle storage part 480. The light-irradiating part 600 may be mounted at the side of the nozzle 473. By mounting the light-irradiating part 600 at the side of the nozzle 473, similarly to the example shown in FIG. 10, the bacteria-removing light can be efficiently irradiated on locations at which water tends to remain and stains tend to occur.

It is favorable to provide a gap such as the opening 482 or the like between the light-irradiating part 600 and the bowl 801. By providing the gap, the light-irradiating part 600 can irradiate the bacteria-removing light on the bowl 801 via the gap.

Figure 12:
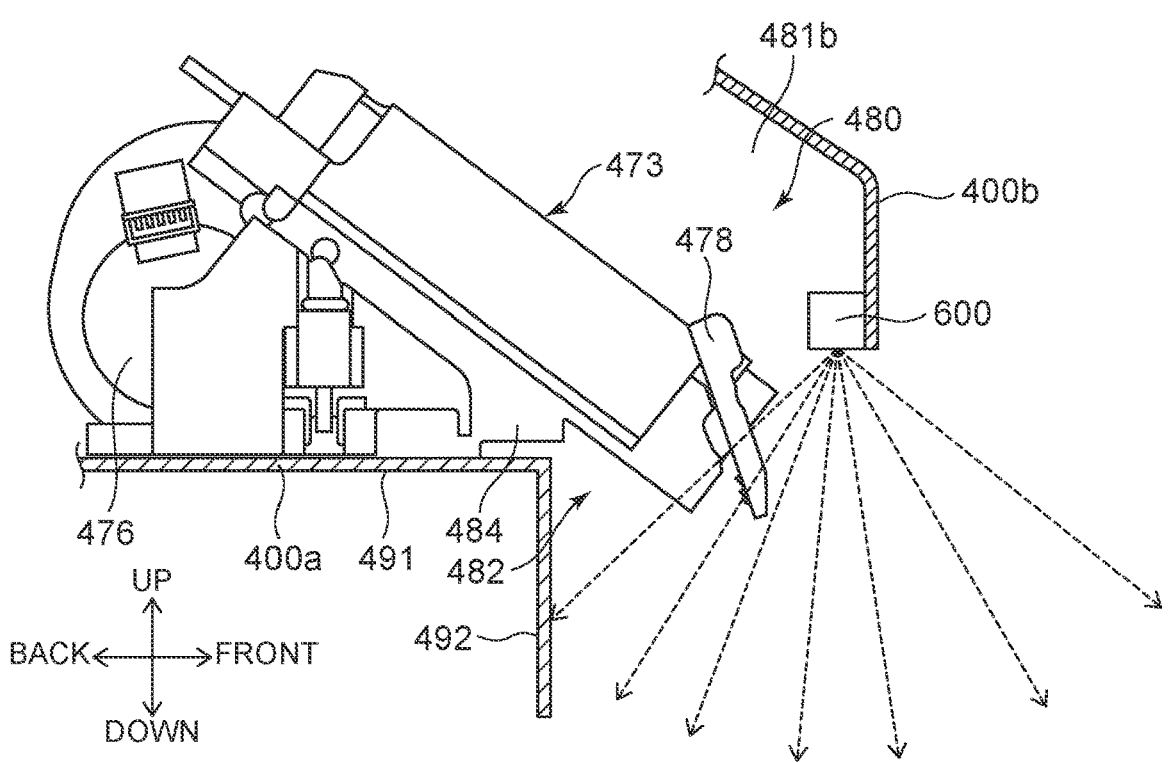
FIG. 12 is a cross-sectional view showing an example of the private part washing nozzle periphery of the toilet device according to the embodiment.

FIG. 12 is a cross-sectional view showing an example of the private part washing nozzle periphery of the toilet device according to the embodiment.

As illustrated in FIG. 12, the bottom part 481*a* may not be disposed below the tip portion of the nozzle 473. That is, at least a part of the bottom part 481*a* positioned below the nozzle storage part 480 may be cut away. The bottom part 481*a* may not be included. By not disposing the bottom part 481*a* below the tip portion of the nozzle 473, the bacteria-removing light can be efficiently irradiated on the part of the bowl 801 positioned directly below the casing 400.

In the example, the case plate 400*a* includes a first part 491 positioned below the nozzle and extending in the longitudinal direction, and a second part 492 extending downward from the front end of the first part 491. The second part 492 forms a part of the inner wall 481 of the nozzle storage part 480. A part of the bacteria-removing light irradiated from the light-irradiating part 600 is irradiated on the second part 492.

Figure 13:
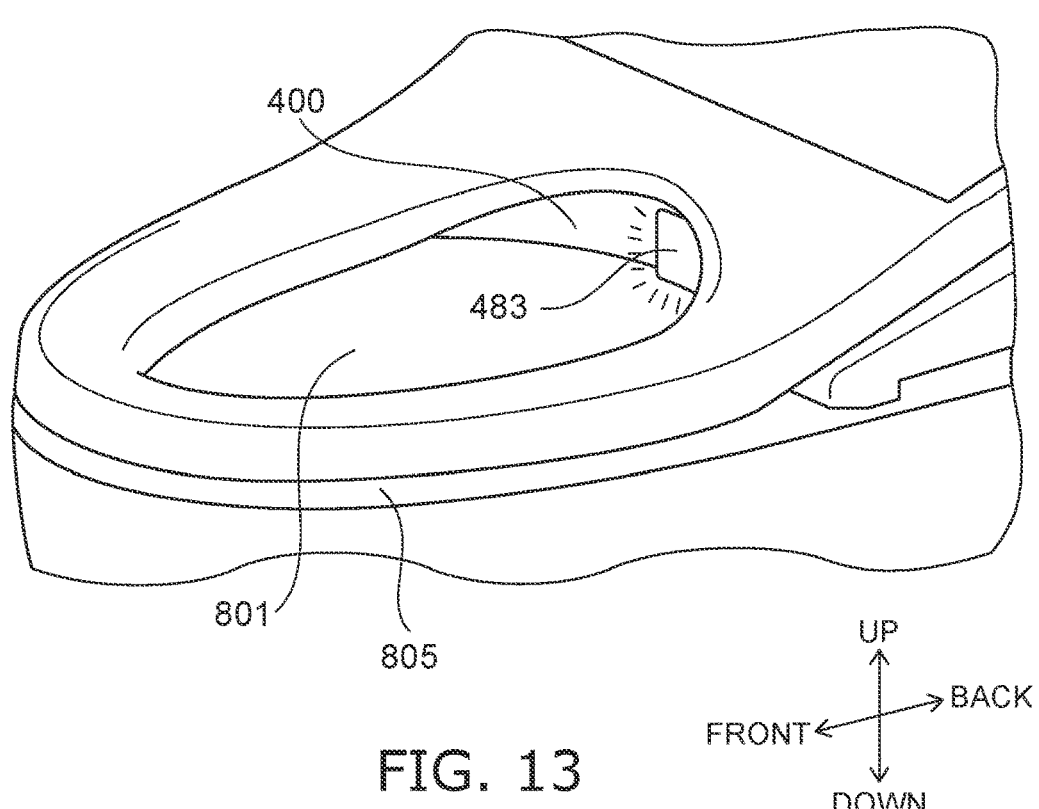
FIG. 13 is an explanatory drawing illustrating an example of the nozzle lid periphery of the toilet device according to the embodiment.

FIG. 13 is an explanatory drawing illustrating an example of the nozzle lid periphery of the toilet device according to the embodiment.

As illustrated in FIG. 13, the vicinity of the nozzle lid 483 can appear luminous to the user by irradiating the bacteria-removing light on the nozzle storage part 480 and the bowl 801 from the light-irradiating part 600 inside the casing 400 with the nozzle lid 483 in the closed state. In such a case, the light-irradiating part 600 irradiates the bacteria-removing light toward the bowl 801 (lower than the rim part 805) to suppress bacterial growth, and irradiates light (e.g., the bacteria-removing light) higher than the rim part 805 to be visible to the user. For example, the light to be visible to the user is emitted directly from the vicinity of the nozzle lid 483 upward past the rim part 805. It is favorable for the luminous flux of the light to be visible to the user (the luminous flux of the light emitted higher than the rim part 805) to be less than the luminous flux of the light emitted toward the bowl 801 (the luminous flux of the light emitted lower than the rim part 805). The luminous flux of the light to be visible to the user (the luminous flux of the light emitted higher than the rim part 805) may be 0.

The total luminous flux is the sum total of the luminous flux of all of the light emitted from the light-irradiating part 600; and the unit of the luminous flux is W. "Visible" means that the light reaches an eye of the user. The intensity of the light irradiated on the surface of the bowl 801 is represented by the irradiance, which is the luminous flux divided by the area. The human eye can detect even an ultra trace amount of irradiance. Therefore, the irradiance necessary to be visible may be less than the irradiance necessary to suppress bacterial growth. Therefore, setting the luminous flux of the light to be visible by being emitted directly from the vicinity of the nozzle lid 483 upward past the rim part 805 to be less than the luminous flux emitted toward the bowl 801, stains can be efficiently suppressed while the light is visible to the user.

The nozzle lid 483 can partially or entirely include a transparent or semi-transparent material. In such a case, examples of the material include, for example, polypropylene, polycarbonate, acrylic, ABS (a copolymer synthetic resin of acrylonitrile, butadiene, and styrene), PBT (poly (butylene terephthalate)), PET (poly(ethylene terephthalate)), etc.

The bacteria-removing light can be irradiated at any timing. The bacteria-removing light may be irradiated when the user is not present in the toilet room, or when the user is present in the toilet room. For example, the bacteria-removing light may be irradiated so that the bacteria-removing light has not less than the integrated irradiance necessary to cause the bacteria count to be not more than the prescribed value over the course of one day, and may be irradiated continuously or discontinuously.

Embodiments may include the following configurations.

Configuration 1

A sanitary washing device mounted on a flush toilet, the flush toilet including a bowl receiving human waste, the sanitary washing device comprising:

a private part washing nozzle configured to advance and retreat, the private part washing nozzle including a water discharge port discharging wash water toward a private part of a user;

a casing including a nozzle storage part, the nozzle storage part being configured to store the private part washing nozzle when the private part washing nozzle is retracted; and a light-irradiating part irradiating a bacteria-removing light, the bacteria-removing light being light having a bacteria-removing action, the bacteria-removing light being irradiated from the light-irradiating part simultaneously on the nozzle storage part and the bowl.

Configuration 2

The sanitary washing device according to configuration 1, wherein an average value of an irradiance of an inner surface of the nozzle storage part irradiated with the bacteria-removing light is greater than an average value of an irradiance of a surface of the bowl irradiated with the bacteria-removing light.

Configuration 3

The sanitary washing device according to configuration 1 or 2, wherein the light-irradiating part is disposed inside the casing.

Configuration 4

The sanitary washing device according to any one of configurations 1 to 3, wherein the bowl includes a bowl back part and a bowl front part, when referenced to an anus washing position, the bowl back part is positioned behind the anus washing position, and the bowl front part is positioned frontward of the anus washing position, and an average value of an irradiance of a surface of the bowl back part irradiated with the bacteria-removing light is greater than an average value of an irradiance of a surface of the bowl front part irradiated with the bacteria-removing light.

Configuration 5

A toilet device, comprising:

the sanitary washing device according to any one of configurations 1 to 4; and the flush toilet.

Thus, according to embodiments, a sanitary washing device and a toilet device can be provided in which bacterial growth at the nozzle storage part and bowl can be suppressed by irradiating bacteria-removing light for a short period of time while preventing a cost increase due to an increase of light-irradiating parts.

The invention has been described with reference to the embodiments. However, the invention is not limited to these embodiments. Any design changes in the above embodiments suitably made by those skilled in the art are also encompassed within the scope of the invention as long as they fall within the spirit of the invention. For example, the shape, the size the material, the disposition and the arrangement or the like of the components included in the sanitary washing device and the toilet device are not limited to illustrations and can be changed appropriately.

The components included in the embodiments described above can be combined to the extent possible, and these combinations are also encompassed within the scope of the invention as long as they include the features of the invention.

What is claimed is:

1. A sanitary washing device mounted on a flush toilet, the flush toilet including a bowl receiving human waste, the sanitary washing device comprising:

a private part washing nozzle configured to advance and retreat, the private part washing nozzle including a water discharge port discharging wash water toward a private part of a user;

a casing including a nozzle storage part, the nozzle storage part being configured to store the private part washing nozzle when the private part washing nozzle is retracted; and a common light-irradiating part irradiating a bacteria-removing light on the nozzle storage part and the bowl, the bacteria-removing light being light having a bacteria-removing action, the bacteria-removing light being irradiated from the light-irradiating part simultaneously on the nozzle storage part and the bowl, the light-irradiating part being disposed inside the casing, the light-irradiating part irradiating the bacteria-removing light on the entire bowl.

2. The sanitary washing device according to claim 1, wherein an average value of an irradiance of an inner surface of the nozzle storage part irradiated with the bacteria-removing light is greater than an average value of an irradiance of a surface of the bowl irradiated with the bacteria-removing light.

3. The sanitary washing device according to claim 1, wherein the bowl includes a bowl back part and a bowl front part, when referenced to an anus washing position, the bowl back part is positioned behind the anus washing position, and the bowl front part is positioned frontward of the anus washing position, and an average value of an irradiance of a surface of the bowl back part irradiated with the bacteria-removing light is greater than an average value of an irradiance of a surface of the bowl front part irradiated with the bacteria-removing light.

4. A toilet device, comprising:

the sanitary washing device according to claim 1; and the flush toilet.

5. A sanitary washing device mounted on a flush toilet, the flush toilet including a bowl receiving human waste, the sanitary washing device comprising:

a private part washing nozzle configured to advance and retreat, the private part washing nozzle including a water discharge port discharging wash water toward a private part of a user;

a casing including a nozzle storage part, the nozzle storage part being configured to store the private part washing nozzle when the private part washing nozzle is retracted; and a common light-irradiating part irradiating a bacteria-removing light on the nozzle storage part and the bowl, the bacteria-removing light being light having a bacteria-removing action, the bacteria-removing light being irradiated from the light-irradiating part simultaneously on the nozzle storage part and the bowl, the nozzle storage part including a bottom part positioned below the private part washing nozzle, the light-irradiating part being disposed between the private part washing nozzle and the bottom part in the casing, the light-irradiating part irradiating the bacteria-removing light toward the front and downward.

6. A sanitary washing device mounted on a flush toilet, the flush toilet including a bowl receiving human waste, the sanitary washing device comprising:

a private part washing nozzle configured to advance and retreat, the private part washing nozzle including a water discharge port discharging wash water toward a private part of a user;

a casing including a nozzle storage part, the nozzle storage part being configured to store the private part washing nozzle when the private part washing nozzle is retracted; and a common light-irradiating part irradiating a bacteria-removing light on the nozzle storage part and the bowl, the bacteria-removing light being light having a bacteria-removing action; and a toilet lid, the bacteria-removing light being irradiated from the light-irradiating part simultaneously on the nozzle storage part and the bowl, the light-irradiating part being disposed at the back surface of the toilet lid, the light-irradiating part irradiating the bacteria-removing light on the entire bowl.

* * * * *